(12) United States Patent
Yamada

(10) Patent No.: US 8,226,676 B2
(45) Date of Patent: Jul. 24, 2012

(54) ULTRASONIC SURGICAL INSTRUMENT

(75) Inventor: Norihiro Yamada, Hachioji (JP)

(73) Assignee: Olympus Medical Systems Corp. (JP)

( * ) Notice: Subject to any disclaimer, the term of this patent is extended or adjusted under 35 U.S.C. 154(b) by 1125 days.

(21) Appl. No.: 12/109,744

(22) Filed: Apr. 25, 2008

(65) Prior Publication Data

US 2008/0208232 A1  Aug. 28, 2008

Related U.S. Application Data

(63) Continuation of application No. PCT/JP2006/321416, filed on Oct. 26, 2006.

(30) Foreign Application Priority Data

Oct. 28, 2005 (JP) ................................ 2005-314324

(51) Int. Cl.
*A61B 17/32* (2006.01)
(52) U.S. Cl. ........... 606/169; 82/904; 310/328; 310/800
(58) Field of Classification Search ................ 606/169, 606/46, 1, 205; 601/2; 310/26, 323.06, 365, 310/311, 328, 371, 366, 800, 334; 604/22; 227/19; 318/119; 82/904
See application file for complete search history.

(56) References Cited

U.S. PATENT DOCUMENTS

| 4,728,843 A * | 3/1988 | Mishiro | 310/325 |
| 6,063,098 A * | 5/2000 | Houser et al. | 606/169 |
| 6,068,647 A | 5/2000 | Witt et al. | 606/205 |
| 6,214,017 B1 | 4/2001 | Stoddard et al. | 606/128 |
| 6,458,142 B1 * | 10/2002 | Faller et al. | 606/169 |
| 2002/0002371 A1 * | 1/2002 | Acker et al. | 606/27 |

FOREIGN PATENT DOCUMENTS

| JP | 2-68047 | 3/1990 |
| JP | 8-117240 | 5/1996 |
| JP | 11-56867 | 3/1999 |
| JP | 2001-286162 | 10/2001 |
| JP | 2003-527940 | 9/2003 |
| JP | 2005-94552 | 4/2005 |
| WO | WO 2004/012615 | 2/2004 |

OTHER PUBLICATIONS

"Notification of Transmittal of translation of the IPRP . . . and accompanying forms" for PCT/JP2006/321416, mailed May 8, 2008, 7 pages.
International Search Report mailed Nov. 28, 2006 in corresponding PCT International Application No. PCT/JP2006/321416.
S. Ashley, "Artificial Muscles," Nikkei Science, Feb. 2004, pp. 56-65.
Seiki Chiba, Electronic Packaging Techniques 2002.1, vol. 18, No. 1, pp. 32-38.
Roy Kornbluh et al., "Medical Application of New Electroactive Polymer Artificial Muscles," Mold Working, vol. 16, No. 10, pp. 631-637, Oct. 2004.

* cited by examiner

*Primary Examiner* — Ryan Severson
*Assistant Examiner* — Tin Nguyen
(74) *Attorney, Agent, or Firm* — Ostrolenk Faber LLP

(57) ABSTRACT

First and second actuators where positive electrodes and negative electrodes are disposed on cylindrical electrostrictive polymers are disposed so as to face each other via a fixing member, a blade inserted into the first actuator is provided on the fixing member, and the blade is ultrasonically vibrated via the fixing member by driving one of the first and second actuators in a stretching and shrinking manner and driving the other in a stretching manner in synchronization with each other.

7 Claims, 15 Drawing Sheets

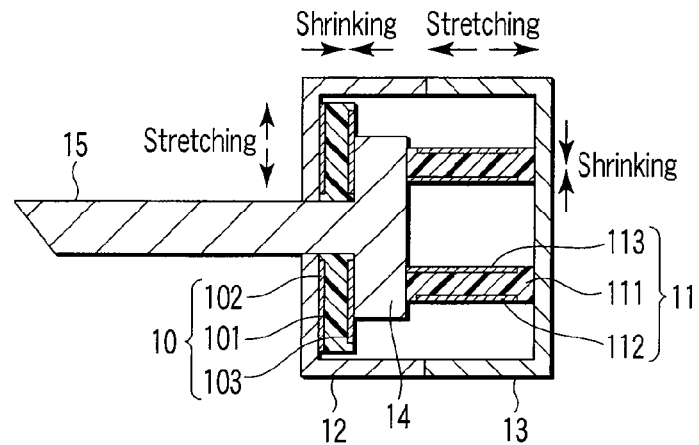
F I G. 4
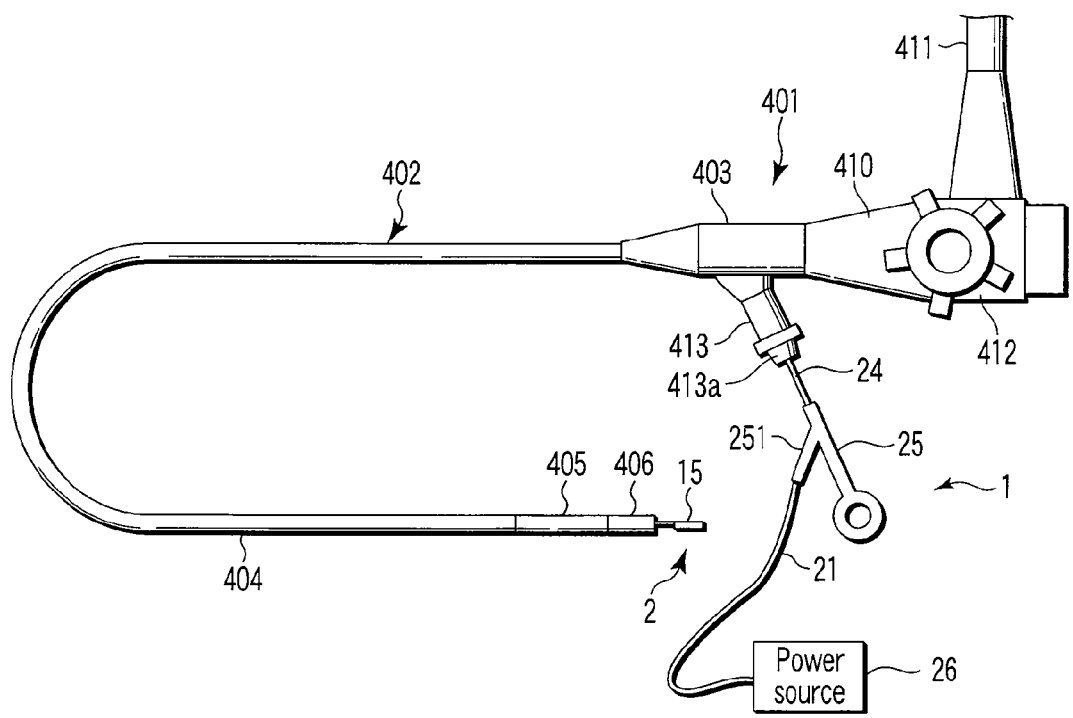
F I G. 5

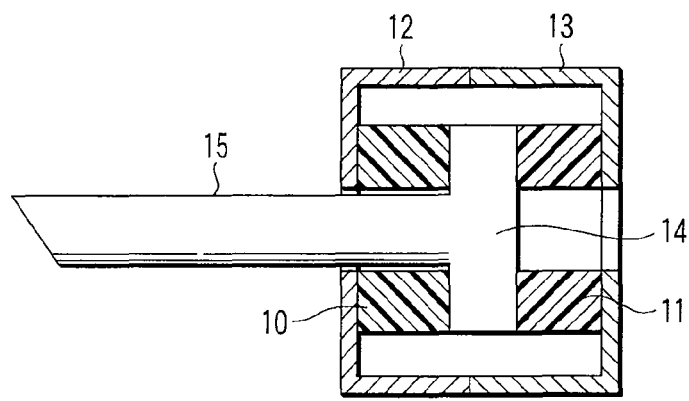
F I G. 11A
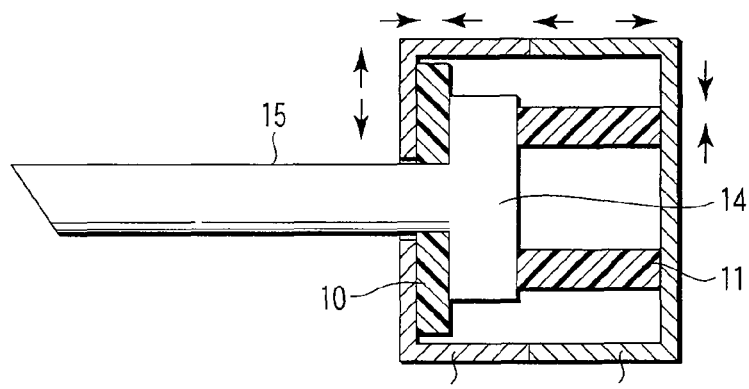
F I G. 11B
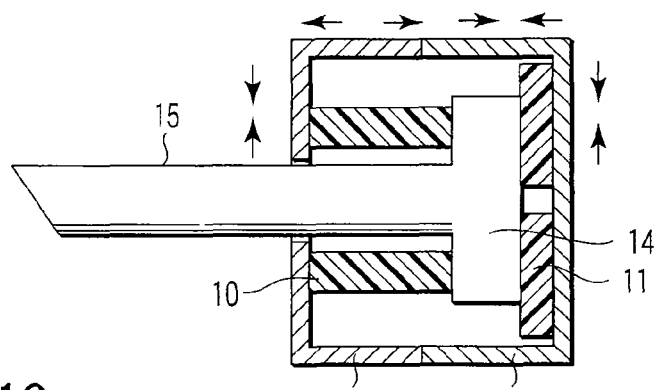
F I G. 11C

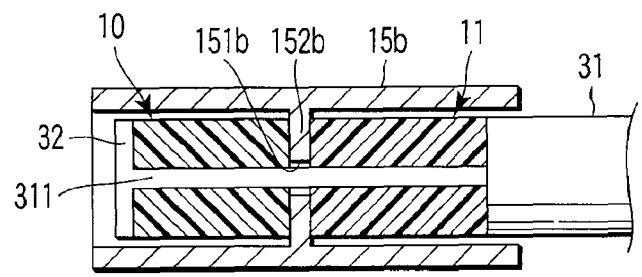
F I G. 18A
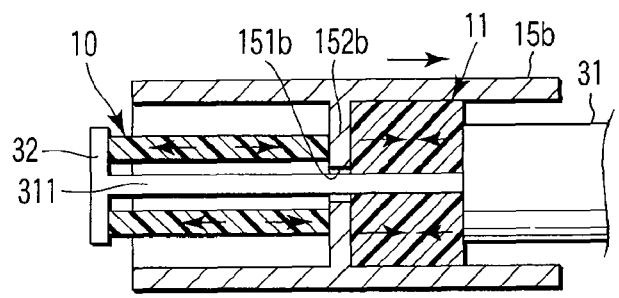
F I G. 18B
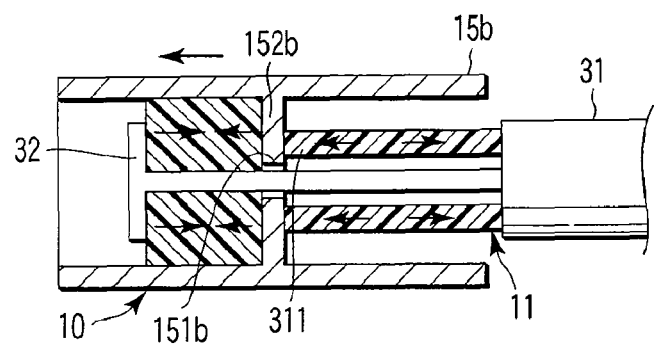
F I G. 18C

ULTRASONIC SURGICAL INSTRUMENT

CROSS REFERENCE TO RELATED APPLICATIONS

This is a Continuation Application of PCT Application No. PCT/JP2006/321416, filed Oct. 26, 2006, which was published under PCT Article 21(2) in Japanese.

This application is based upon and claims the benefit of priority from prior Japanese Patent Application No. 2005-314324, filed Oct. 28, 2005, the entire contents of which are incorporated herein by reference.

BACKGROUND OF THE INVENTION

1. Field of the Invention

The present invention relates to an ultrasonic surgical instrument used for clotting/incising with respect to a body tissue in, for example, a surgical procedure.

2. Description of the Related Art

When an abdomen of a patient is incised and undergoes a surgical operation or when a surgical operation is conducted by utilizing an endoscope, an ultrasonic surgical instrument is generally used as means for clotting and incising with respect to body tissue. The ultrasonic surgical instrument includes an ultrasonic transducer generating ultrasonic vibration and an ultrasonic probe configuring a surgical section. Ultrasonic vibration generated by the ultrasonic transducer is amplified and transmitted to the ultrasonic probe, where clotting/incising with respect to a body tissue is performed by utilizing the ultrasonic vibration.

As an ultrasonic transducer used in the ultrasonic surgical instrument, an apparatus having a bolt-tightening Langevin type transducer structure (for example, see U.S. Pat. No. 6,068,647 [Patent Document 1]) or an apparatus having a magnetostriction type transducer structure (for example, see U.S. Pat. No. 6,214,017 [Patent Document 2]) are known. The structure of the bolt-tightening Langevin type transducer has such a configuration that piezoelectric elements and electrodes are alternately stacked and the stacked body is arranged between a horn and a backing plate in a fastening manner. The structure of the magnetostriction type transducer has such a configuration that magnetostriction material is wound by a coil.

Recently, as a candidate of material for artificial muscle, it is considered that electrostrictive polymer such as silicon resin or acrylic resin which is polymer material with electric field response called "dielectric elastomer" is used. For example, see Nikkei Science, February 2004 issue, pp. 56-65 (Non-Patent Document 1), Electronic Packaging Techniques 2002.1 (Vol. 18 No. 1) pp. 32-38 (Non-Patent Document 2), and Mold Working: Vol. 16 No. 10 2004 pp. 631-637 (Non-Patent Document 3). The electrostrictive polymer includes electrodes formed on both faces thereof in a thin film manner. When voltage is applied between both the electrodes, such an action that one face side is shrunk and the other face side is stretched occurs. In an actuator using such an electrostrictive polymer, the electrostrictive polymer shrinks and stretches to generate desired driving force according to cyclic application of voltage between the electrodes.

As a usage example of such an actuator utilizing an electrostrictive polymer, application to a prosthesis such as an artificial hand, an artificial leg, a haptic, a soft skin allowing sensing, or a pump for diagnosing blood or the like, or medical equipment has been researched (for example, see Non-Patent Document 3).

BRIEF SUMMARY OF THE INVENTION

According to a first aspect of the present invention, an ultrasonic surgical instrument including a surgical unit which generates ultrasonic vibration to conduct a procedure of a site to be operated on and driving means for driving the surgical unit, wherein the driving means comprises: a first actuator provided with a first actuator main body formed of electrostrictive polymer and at least one pair of electrodes which are arranged on the first actuator main body so as to be separated from each other, where when voltage is applied between the electrodes, the electrostrictive polymer is driven in a stretching and shrinking manner; a second actuator provided with a second actuator main body formed of electrostrictive polymer and at least one pair of electrodes which are arranged on the second actuator main body so as to be separated from each other, where when voltage is applied between the electrodes, the electrostrictive polymer is driven in a stretching and shrinking manner; a fixing member which is coupled to the surgical unit and interposed between the first actuator and the second actuator; and power source means for alternately repeating an operation for driving one electrostrictive polymer of the first and second actuators in a shrinking manner and an operation for driving the other electrostrictive polymer in a stretching manner cyclically to ultrasonically vibrate the surgical unit via the fixing member at a time of driving the first and second actuators.

Preferably, the driving means includes a casing accommodating the first actuator and the second actuator, and the first actuator and the second actuator are accommodated in the casing in a stretchable and shrinkable manner.

Preferably, the first actuator includes a first actuator main body formed of electrostrictive polymer with a cylindrical shape and a pair of electrodes disposed on both end portions with the cylindrical shape of the first actuator main body, the second actuator includes a second actuator main body formed of electrostrictive polymer with a cylindrical shape and a pair of electrodes disposed on an outer peripheral face and an inner peripheral face with the cylindrical shape of the second actuator main body, respectively; the surgical unit includes a shaft unit inserted into an inner space portion of the cylindrical shape of the first actuator main body of the first actuator, the shaft unit including a distal end portion and a proximal end portion, and the distal end portion contacting with the site to be operated on to conduct a procedure of the site to be operated on, and the fixing member is interposed between a proximal end portion of the first actuator main body of the first actuator and a distal end portion of the second actuator main body of the second actuator, and the proximal end portion of the shaft unit of the surgical unit is coupled to a shaft center portion of the fixing member.

Preferably, the first actuator includes a first positive electrode disposed on a front end face with the cylindrical shape of the first actuator main body and a first negative electrode disposed on a rear end face with the cylindrical shape of the first actuator main body and fixed in a contacting state with the fixing member, the second actuator includes a second positive electrode disposed on an outer peripheral face with the cylindrical shape of the second actuator main body and fixed in a non-contacting state with the fixing member, and a second negative electrode disposed on an inner peripheral face with the cylindrical shape of the second actuator main body and fixed in a contacting state with the fixing member, the second electrode is electrically connected to the first positive electrode via a positive wiring, and the second electrode is electrically connected to the first negative electrode via the fixing member.

Preferably, the power source means applies AC voltages having a phase difference of 180° between the electrodes of the first actuator and between the electrodes of the second actuator in a synchronizing manner.

Preferably, the first actuator and the second actuator have each a stacked structure where a polymer film formed of electrostrictive polymer and a plurality of inner electrodes are alternately stacked.

According to another aspect of the present invention, an ultrasonic surgical instrument comprising: an insertion unit having a distal end portion and a proximal end portion and inserted into a channel of an endoscope; a surgical unit disposed at the distal end portion of the insertion unit and ultrasonically vibrating to conduct a procedure of a site to be operated on; and driving means for driving the surgical unit, where the ultrasonic surgical instrument conducts a procedure of the site to be operated on by ultrasonic vibration of the surgical unit under observation conducted by the endoscope, wherein the insertion unit is provided with a flexible sheath having a distal end portion and a proximal end portion, the distal end portion of the sheath is connected with the surgical unit, an operation unit for operating the surgical unit is disposed on the proximal end portion of the sheath, and the driving means comprises: a first actuator provided with a first actuator main body formed of electrostrictive polymer and at least one pair of electrodes which are arranged on the first actuator main body so as to be separated from each other to achieve insulation arrangement, where when voltage is applied between the electrodes, the electrostrictive polymer is driven in a stretching and shrinking manner; a second actuator provided with a second actuator main body formed of electrostrictive polymer and at least one pair of electrodes which are arranged on the second actuator main body so as to be separated from each other to achieve insulation arrangement, where when voltage is applied between the electrodes, the electrostrictive polymer is driven in a stretching and shrinking manner; a fixing member which is coupled to the surgical unit and interposed between the first actuator and the second actuator; and power source means for alternately repeating an operation for driving one electrostrictive polymer of the first and second actuators in a shrinking manner and an operation for driving the other electrostrictive polymer in a stretching manner cyclically to ultrasonically vibrate the surgical unit via the fixing member at a time of driving the first and second actuators.

Preferably, the surgical unit comprises: a cylindrical blade having a distal end portion and a proximal end portion, the blade having a suction hole communicating with an inner cavity of the blade at the distal end portion, and a suction tube having a distal end portion and a proximal end portion and disposed inside the sheath, the distal end portion of the tube communicating with the inner cavity of the blade, and the proximal end portion of the tube being extended from the operation unit to the outside to be connected to a suction pump.

Preferably, the surgical unit comprises: a cylindrical blade having a distal end portion and a proximal end portion, in which the driving means is housed, a distal end cover member having a distal end portion and a proximal end portion, the proximal end portion of the distal end cover member being coupled to the distal end portion of the sheath, a forceps piece rotatably coupled to the distal end cover member and supported in openable and closable to the blade, a forceps driving unit driving the forceps piece such that the forceps piece is opened and closed to the blade, an operation wire having a distal end portion and a proximal end portion, provided inside the sheath so as to be movable in a center line direction of the sheath, and operating the forceps driving unit, and a handle provided on the operation unit, driving the forceps driving unit via the operation wire, and driving the forceps piece such that the forceps piece is opened and closed to the blade.

Preferably, the blade is provided with a cylindrical casing and a partition wall disposed inside the casing to partition an inner space portion of the casing into a front portion and a rear portion, the partition wall having an insertion hole at a central portion of the casing, the distal end cover member includes a fixing shaft unit inserted into the casing and extended to a front end portion side of the casing via the insertion hole of the partition wall, and in the driving means, the first actuator and the second actuator are disposed in an inner space portion of the casing to face each other via the partition wall, and the driving means includes assembling means for assembling the first actuator and the second actuator to the fixing shaft member and the distal end cover member.

BRIEF DESCRIPTION OF THE SEVERAL VIEWS OF THE DRAWING

FIG. 4 is a view showing for explaining a stretching and shrinking action of the first actuator and the second actuator of the ultrasonic surgical instrument according to the first embodiment;

FIG. 5 is a characteristic view showing a state where the ultrasonic surgical instrument according to the first embodiment has been attached to an insertion unit of an endoscope;

FIG. 11A is an explanatory view showing initial states of the first and second actuators in the third modification example;

FIG. 11B is an explanatory view showing a state where the first actuator has been driven in a shrinking manner and the second actuator has been driven in a stretching manner in the third modification example;

FIG. 11C is an explanatory view showing a state where the first actuator has been driven in a stretching manner and the second actuator has been driven in a shrinking manner in the third modification example;

FIG. 18A is an explanatory view showing an initial state of an actuator of the ultrasonic surgical instrument according to the third embodiment;

FIG. 18B is an explanatory view showing a state where a first actuator has been driven in a shrinking manner and a second actuator has been driven in a stretching manner in the ultrasonic surgical instrument according to the third embodiment; and FIG. 18C is an explanatory view showing a state where the first actuator has been driven in a stretching manner and the second actuator has been driven in a shrinking manner in the ultrasonic surgical instrument according to the third embodiment.

DETAILED DESCRIPTION OF THE INVENTION

Embodiments of the present invention will be explained in detail below with reference to the drawings.

First Embodiment

Figure 1:
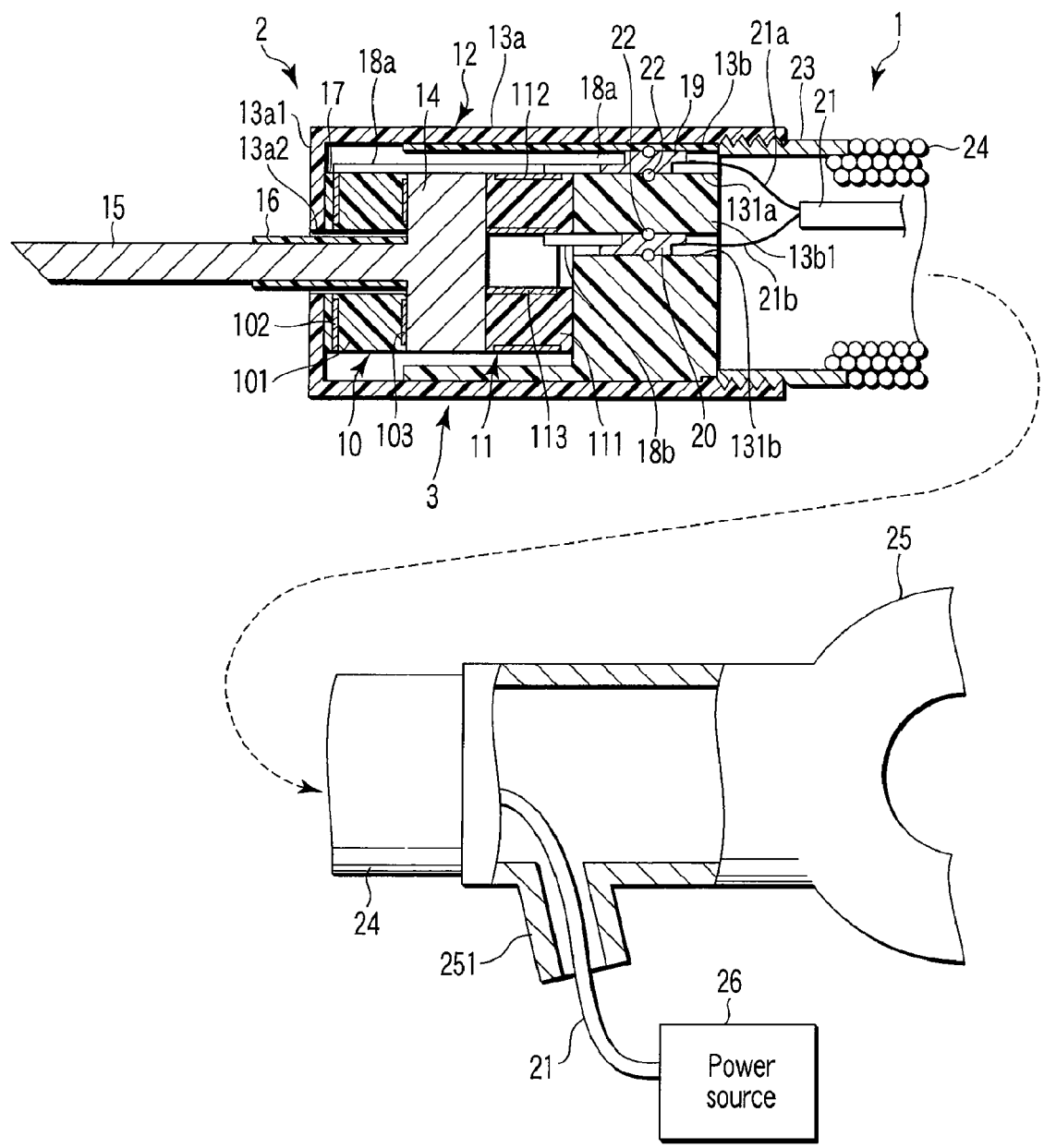
FIG. 1 is a schematic configuration view of a main section showing a portion of an ultrasonic surgical instrument according to a first embodiment of the present invention in a partially sectional manner.

FIG. 1 to FIG. 6 show a first embodiment of the present invention. FIG. 1 shows a schematic configuration view of a main section of an ultrasonic surgical instrument 1 used together with an endoscope 401 (FIG. 5).

Figure 6:
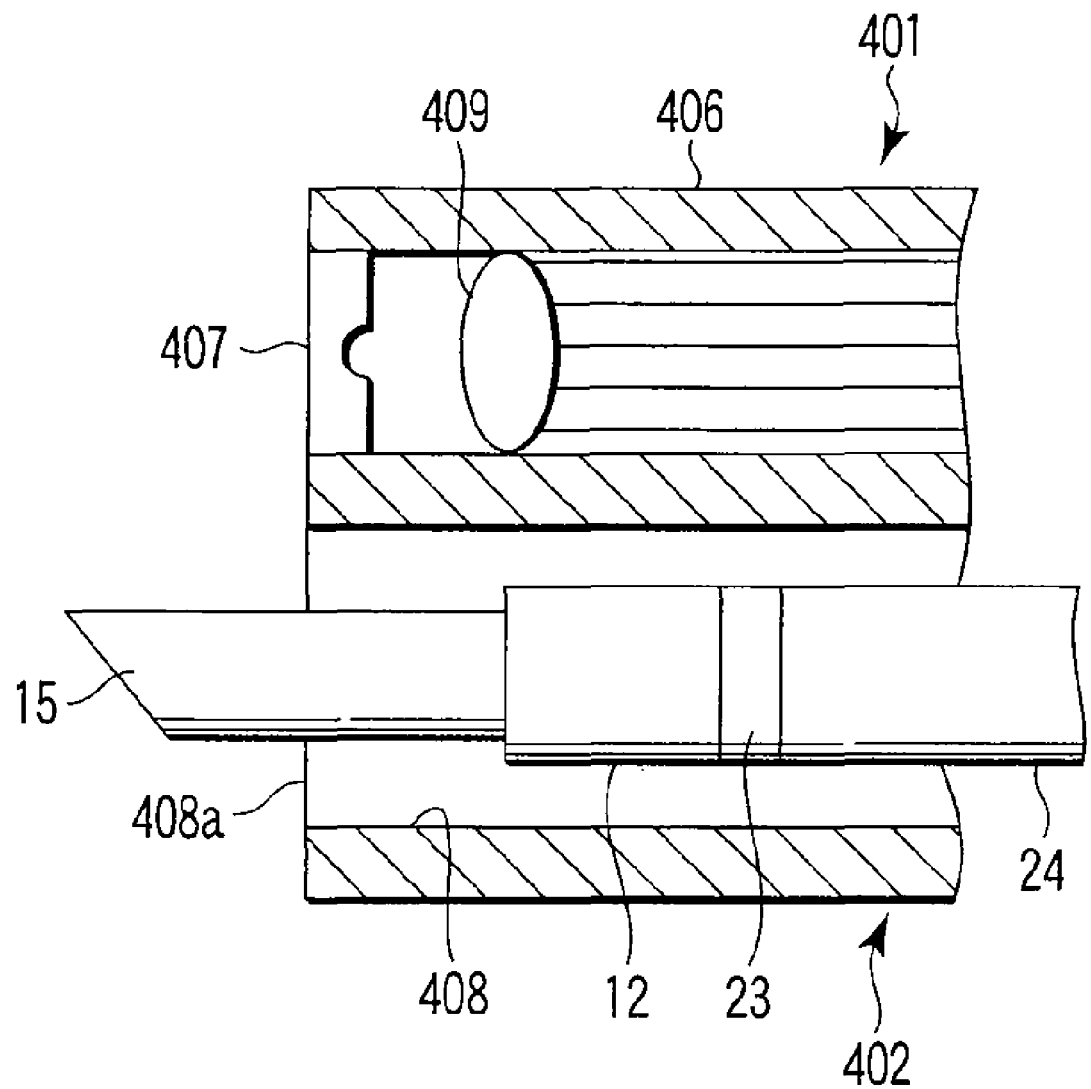
FIG. 6 is a view showing a state where a blade, first and second cases, and sheathes of the ultrasonic surgical instrument according to the first embodiment have been inserted into a channel of the insertion unit of the endoscope in enlarged manner.

FIG. 5 shows a schematic configuration of the endoscope 401. The endoscope 401 includes an elongated insertion unit 402 inserted into a human body and an operation unit 403 coupled to a proximal end portion of the insertion unit 402. The insertion unit 402 includes an elongated flexible pipe portion 404, a bending portion 405 whose proximal end portion is coupled to a distal end portion of the flexible pipe portion 404, and a distal end hard portion 406 whose proximal end portion is coupled to a distal end portion of the bending portion 405. The bending portion 405 can be operated from its ordinary straight state extending straightly to a bent shape in a bending manner. As shown in FIG. 6, an illumination lens of an illumination optical system (not shown), an objective lens 407 of an observation optical system, a distal end opening portion 408a of a surgical tool insertion channel 408, a gas/water feeding nozzle (not shown), and the like are disposed on a distal end face of the distal end hard portion 406.

An imaging device 409 such as a CCD, a connection circuit board for the imaging device 409, and the like are fixed at the distal end hard portion 406 behind the objective lens 407. Incidentally, a distal end portion of an image guide fiber (not shown) is fixed instead of the imaging device 409 and the endoscope 401 may be used for an electronic scope or a fiber scope may be used instead of the endoscope 401. Further, a distal end portion of the surgical tool insertion channel 408, distal end portions of a gas feeding tube and a water feeding tube connected to the gas feeding/water feeding nozzle and the like may be fixed at the distal end hard portion 406.

A handle portion 410 grasped by an operator is disposed on the operation unit 403. The handle portion 410 is connected with a proximal end portion of a universal cord 411. A connector portion connected to a light source apparatus (not shown), a video processor (not shown), or the like is coupled to a distal end portion of the universal cord 411.

Further, a bending operation knob 412 operating the bending portion 405 in a bending manner, a suction button, a gas feeding/water feeding button, various switches for endoscope photographing, a surgical tool insertion ferrule 413, and the like are provided on the operation unit 403. A surgical tool insertion port 413a coupled to a proximal end portion of the surgical tool insertion channel 408 disposed in the insertion unit 402 is provided in the ferrule 413 for surgical tool insertion. After the ultrasonic surgical instrument 1 according to the embodiment which is a surgical tool for an endoscope is inserted from the surgical tool insertion port 413a of the endoscope 401 into the surgical tool insertion channel 408 and it is operated up to the distal end hard portion 406 side in a pushing manner, it is protruded from a distal end portion opening portion 408a of the surgical tool insertion channel 408 to the outside.

As shown in FIG. 1, the ultrasonic surgical instrument 1 includes an elongated flexible sheath 24 such as a tightly-wound coil, and an operation unit 25 coupled to a proximal end portion of the sheath 24. A distal end surgical unit 2 is coupled to a distal end portion of the sheath 24 via a coupling tube 23. A blade 15 which is a surgical element for carrying out a procedure such as incising of a body tissue/arrest of bleeding, or the like and a driving unit 3 for ultrasonically vibrating the blade 15 are provided at the distal end surgical unit 2.

The driving unit 3 includes a casing 12, a blade fixing member 14, and first and second actuators 10, 11. The casing 12 includes a first case 13a disposed at a front side and a second case 13b positioned at a rear side and assembled in a state that it has been inserted into the first case 13a.

The first case 13a is formed of a cylindrical body. A front face of the first case 13a is closed by a front face plate 13a1. A blade insertion hole 13a2 is formed at a central portion of the front face plate 13a1. A distal end portion of the coupling tube 23 at the distal end portion of the sheath 24 is coupled to a rear end portion of the first case 13a via a screw unit.

The second case 13b is formed of a cylindrical body. A rear face of the second case 13b is closed by a rear face plate 13b1. Two insertion holes 131a, 131b for metal plate attachment for wiring are formed in the rear face plate 13b1.

The blade 15 is formed integrally with, for example, the abovementioned blade fixing member 14. The blade 15 is protruded forward from the blade insertion hole 13a2 in the abovementioned first case 13a. The blade fixing member 14 is made of electrically conductive metal material.

The blade fixing member 14 together with the first and second actuators 10, 11 is accommodated in two cases, that is the first and second casing 13a, 13b. Here, the first and second actuators 10, 11 are disposed in the first and second cases 13a, 13b to face each other via the blade fixing member 14 which is an electrically conductive member.

Incidentally, when the first and second cases 13a, 13b are made of metal material, an outer peripheral portion of the blade 15 is covered with, for example, an insulation tube 16, so that the blade 15 is held in a state that insulation is maintained between the blade 15 and the first case 13a.

The first and second actuators 10, 11 comprise electrostrictive polymer actuators configuring an ultrasonic transducer, respectively. The first actuator 10 of these actuators has such a configuration that stretchable flexible positive electrode 102 and negative electrode 103 are attached on a both end faces of an electrostrictive polymer 101 with a cylindrical shape so as to be separated from each other. Here, the positive electrode 102 is disposed on a front end face of the electrostrictive polymer 101 contacting with the first case 13a, while the negative electrode 103 is disposed on a rear end face of the electrostrictive polymer 101 contacting with the abovementioned blade fixing member 14. The first actuator 10 is configured such that an insulation ring 17 is interposed between the positive electrode 102 and the first case 13a and insulation between the first actuator 10 and the first case 13a is maintained. The blade 15 is inserted into a cylindrical hollow space portion of the electrostrictive polymer 101 of the first actuator 10.

The abovementioned second actuator 11 has such a configuration that stretchable flexible positive electrode 112 and negative electrode 113 are attached on an outer peripheral face and an inner peripheral face of a electrostrictive polymer 111 with a cylindrical shape so as to be separated from each other. Here, the positive electrode 112 is disposed on the outer peripheral face of the electrostrictive polymer 111, while the negative electrode 113 is disposed on the inner peripheral face of the electrostrictive polymer 111. The negative electrode 113 is electrically connected in a state that the positive electrode 112 contacts with the blade fixing member 14 like the first actuator 10. Further, the second actuator 11 is configured such that the positive electrode 112 is electrically connected to the positive electrode 102 of the first actuator 10 via a positive wiring 18a. Similarly, the negative electrode 113 of the second actuator 11 is electrically connected to the negative electrode 103 of the abovementioned first actuator 10 via the blade fixing member 14.

The electrostrictive polymers 101, 111 of the first and second actuators 10, 11 are capacitors having elasticity like rubber and the electrostrictive polymer is called electrostatic elastomer. These electrostrictive polymers 101, 111 are called dielectric elastomer as shown in the previously described Non-Patent Document 2, and they are formed in a cylindrical shape made of resin material such as, for example, acrylic, silicon, or polyurethane. As the positive electrodes 101, 102, and the negative electrodes 103, 113, electrodes formed in a film by using, for example, photolithography, carbon electrodes obtained by spraying mixture of binder and carbon fine particles, or the like are used.

A positive metal plate 19 and a negative metal plate 20 are disposed in one electrode insertion hole 131a in the second case 13b and the other electrode insertion hole 131b of the second case 13b, respectively. O-rings 22 are attached on outer peripheral faces of the positive metal plate 19 and the negative metal plate 20, respectively. The positive metal plate 19 and the negative metal plate 20 are accommodated in two insertion holes 131a, 131b in the second case 13b via, for example, the O-rings 22 in a sealing manner, respectively.

The positive electrode 112 in the abovementioned second actuator 11 is electrically connected to the positive metal plate 19 in the second case 13b via a positive wiring 18a. The positive metal plate 19 is connected with a positive leading wiring 21a of the wiring cable 21.

The negative electrode 113 in the abovementioned second actuator 11 is electrically connected to the negative metal plate 20 in the second case 13b via a negative wiring 18b. The negative metal plate 20 is connected with a negative leading wiring 21b of the wiring cable 21.

The abovementioned wiring cable 21 extends in the operation unit 25 side through the sheath 24. A wiring cable pulling-out port 251 is provided in the operation unit 25. The wiring cable 21 is pulled out from the pulling-out port 251 of the operation unit 25. A power source 26 is connected to the wiring cable 21 pulled out from the pulling-out port 251. The power source 26 configures power source means for supplying desired voltage cyclically.

Figure 2A:
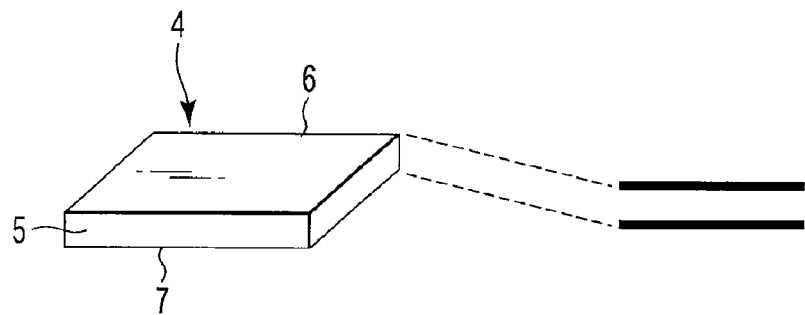
FIG. 2A is a schematic configuration view showing a main section shown for explaining a first actuator and a second actuator of the ultrasonic surgical instrument according to the first embodiment.
Figure 2B:
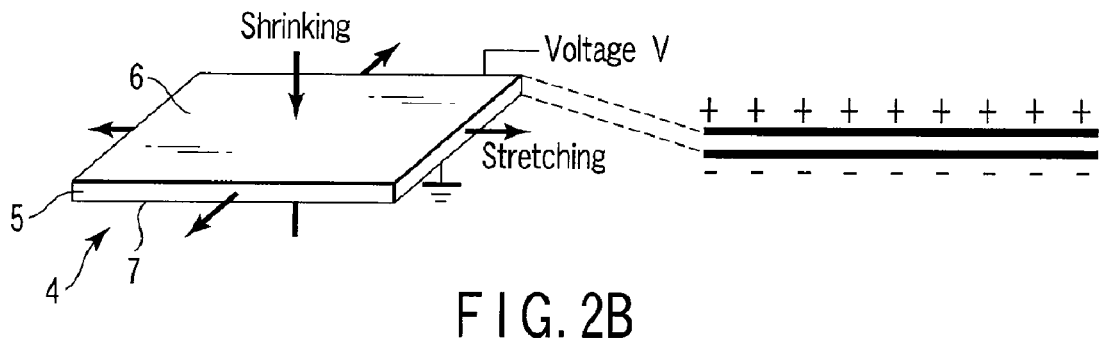
FIG. 2B is a schematic configuration view of a main section shown for explaining an operation principle of the first actuator and the second actuator of the ultrasonic surgical instrument according to the first embodiment.
Figure 3:
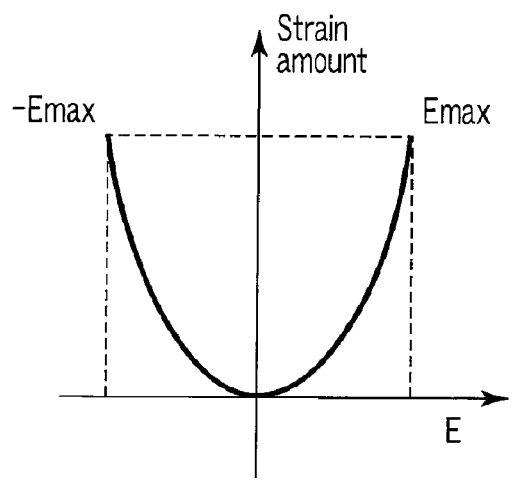
FIG. 3 is a diagram showing a relationship between electric field E and strain of the actuator shown in FIG. 2B.

Next, a driving principle of the abovementioned first and second actuators 10, 11 will be explained with reference to FIGS. 2A, 2B, and FIG. 3. FIG. 2A shows a plate-like actuator model 4 utilizing an electrostrictive polymer, as shown in Non-Patent Document 3 previously described. The actuator model 4 has a positive electrode 6 formed on one face of the plate-like electrostrictive polymer 5 and a negative electrode 7 formed on the other face thereof. Voltage is applied between the positive electrode 6 and the negative electrode 7 at a desired cycle. In this case, attracting force is generated between the positive electrode 6 and the negative electrode 7 of the electrostrictive polymer 5 in synchronism with the cycle of voltage. Therefore, as shown in FIG. 2B, the electrostrictive polymer 5 is shrunk in an inter-electrode direction and it is stretched in a direction orthogonal thereto. It has been confirmed that a strain coefficient is proportional to a square of electric field E applied as shown in FIG. 3 and it reaches several tens percentages to three hundreds percentages or more.

The abovementioned first and second actuators 10, 11 operate based upon the operation principle in the following manner. That is, voltage from the power source 26 is applied between the positive electrodes 102, 112 and the negative electrodes 103, 113 at a desired cycle at a time of an actuation of the first and second actuators 10, 11. At this time, as shown in FIG. 4, the electrostrictive polymer 101 of the first actuator 10 is shrunk in a thickness direction of the electrostrictive polymer 101 (in a direction between the electrodes 102 and 103) and stretched in a direction (a direction of plate face) orthogonal to the thickness direction of the electrostrictive polymer 101 in synchronism with a cycle of voltage. The electrostrictive polymer 111 of the second actuator 11 is shrunk in a diametrical direction of a cylinder of the electrostrictive polymer 111 and stretched in an axial direction of the cylinder of the electrostrictive polymer 111 perpendicular to the diametrical direction of the cylinder. Thereby, regarding the blade 15 provided on the blade fixing member 14, respective shrinking and stretching actions of the first actuator 10 and the second actuator 11 which are independent from each other are alternately repeated cyclically so that the blade 15 is ultrasonically vibrated in linkage with the actions.

As shown in FIG. 5, the ultrasonic surgical instrument 1 is inserted into the surgical tool insertion channel 408 via the surgical tool insertion ferrule 413 of the operation unit 403 of the endoscope 403 at a time of using the ultrasonic surgical instrument 1 according to the first embodiment. As shown in FIG. 6, the blade 15 at the distal end surgical unit 2 of the ultrasonic surgical instrument 1 is protruded from the distal end opening portion 408a of the surgical tool insertion channel 408 to the outside. In this state, voltage from the abovementioned power source 26 is applied to the pulse electrodes 102, 112 and the negative electrodes 103, 113 of the respective electrostrictive polymers 101, 111 in the first and second actuators 10, 11 positioned in the distal end surgical unit 2. Thereby, the first actuator 10 and the second actuator 11 are independently driven in a shrinking manner and driven in a stretching manner so that the blade 15 is ultrasonically vibrated, as shown in FIG. 4 described above. Therefore, a procedure of incising of a body tissue/arrest of bleeding, or the like using the blade 15 is made possible.

Next, an operation of the present embodiment with the abovementioned configuration will be explained. When a procedure such as incising of a body tissue/arrest of bleeding or the like is performed using the ultrasonic surgical instrument 1 with the abovementioned configuration, the insertion unit 402 of the endoscope 401 is first inserted into a body cavity. At this time, an observation image in the body cavity entered through the objective lens 407 of the observation optical system of the endoscope 401 is picked up by the imaging device 409, the image is observed through a screen displayed on a monitor (not shown), and an affected area is confirmed. In a state that the affected area has been confirmed by the endoscope 401, the ultrasonic surgical instrument 1 is inserted into the surgical tool insertion channel 408 through the surgical tool insertion ferrule 413 of the operation unit 403 of the endoscope 401. As shown in FIG. 6, the blade 15 at the distal end surgical unit 2 of the ultrasonic surgical instrument 1 is protruded from the distal end opening portion 408*a* of the surgical tool insertion channel 408 to the outside.

Next, the operation unit 25 is operated while the affected area is observed by the endoscope 401, so that the blade 15 is adjusted to a procedure site while it is moved back and forth. Thereafter, ultrasonic generation operation means (not shown) of the ultrasonic surgical instrument 1, for example, a foot switch, a hand switch, or the like is operated. Here, voltage from the power source 26 is applied to each of the positive electrodes 102, 112, and the negative electrodes 103, 113 of the first and second actuators 10, 11 at a desired cycle. Thereby, an operation where the respective electrostrictive polymers 101, 111 of the first and second actuators 10, 11 are independently driven in a shrinking manner and an operation where they are independently driven in a stretching manner are alternately repeated cyclically in synchronism with a supplying cycle of voltage from the power source 26. Thereby, the blade 15 is ultrasonically vibrated so that a procedure of incising of a body tissue/arrest of bleeding is performed.

With the abovementioned configuration, the following effects can be obtained. That is, in the abovementioned ultrasonic surgical instrument 1, the first actuator 10 and the second actuator 11 are disposed in the casing 12 so as to face each other via the blade fixing member 14. Such a configuration is adopted that the blade 15 extending through the first actuator 10 is provided on the blade fixing member 14 and the blade 15 is ultrasonically vibrated via the blade fixing member 14 by driving one of the first and second actuators 10, 11 in a shrinking manner and driving the other thereof in a stretching manner in synchronism with each other.

Thereby, one of the first and second actuators 10, 11 is shrunk at a strain coefficient of several tens percentages to several hundreds percentages and the other thereof is stretched at a strain coefficient of several tens percentages to several hundreds percentages so that the blade 15 is ultrasonically vibrated, as shown in Non-Patent Documents 1 and 3 previously described. Thereby, it is made possible to ultrasonically vibrate the blade 15 at large amplitude. Therefore, a blade 15 having high procedure ability can be realized using a small-sized actuator, and size-reduction of an apparatus can be achieved.

In the above explanation, the case where the positive electrode 102 and the negative electrode 103 are provided on both side faces of the electrostrictive polymer 101 of the first actuator 10 and the positive electrode 112 and the negative electrode 113 are provided on the inner peripheral face and the outer peripheral face of the electrostrictive polymer 111 of the second actuator 11 has been explained, but the electrode structure of the present invention is not limited to this structure.

Figure 7A:
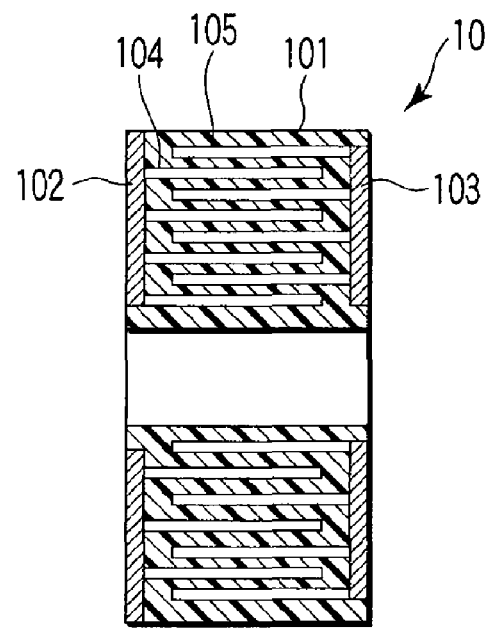
FIG. 7A is a view showing an electrode structure of a first actuator in a first modification example of the ultrasonic surgical instrument according to the first embodiment.
Figure 7B:
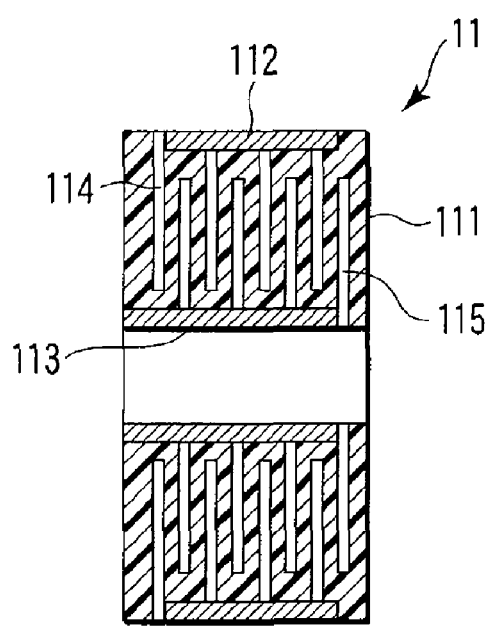
FIG. 7B is a view showing an electrode structure of a second actuator in the first modification example of the ultrasonic surgical instrument according to the first embodiment.

FIGS. 7A and 7B show a first modification example of the ultrasonic surgical instrument 1 of the first embodiment. FIG. 7A shows an electrode structure of a first actuator 10 of the present modification example, and FIG. 7B shows an electrode structure of a second actuator 11 of the present modification example.

In the electrode structure of the first actuator 10 of the present modification example, a plurality of positive internal electrodes 104 and a plurality of negative internal electrodes 105 extending in parallel in the same direction as a center line of the cylinder of the electrostrictive polymer 101 are disposed in the electrostrictive polymer 101. Here, a stack structure where the positive internal electrodes 104, the negative internal electrodes 105, and films of the electrostrictive polymer 101 are alternately stacked is formed. Further, the plurality of positive internal electrodes 104 is electrically connected to the positive electrode 102 in such a state that they are embedded in the electrostrictive polymer 101 at predetermined intervals. Similarly, the plurality of negative internal electrodes 105 is electrically connected to the negative electrode 103 in such a state that they are embedded in the electrostrictive polymer 101 at predetermined intervals.

In the electric structure of the second actuator 11 of the present modification example, a plurality of positive internal electrodes 114 and a plurality of negative internal electrodes 115 extending in a direction perpendicular to a center line of the cylinder of the electrostrictive polymer 101 are disposed in the electrostrictive polymer 111. Here, a stack structure where the positive internal electrodes 114, the negative internal electrodes 115, and films of the electrostrictive polymer 111 are alternately stacked is formed. Further, the plurality of positive internal electrodes 114 is electrically connected to the positive electrode 112 in such a state that they are embedded in the electrostrictive polymer 111 at predetermined intervals. Similarly, the plurality of negative internal electrodes 115 is electrically connected to the negative electrode 113 in such a state that they are embedded in the electrostrictive polymer 111 at predetermined intervals.

Figure 8:
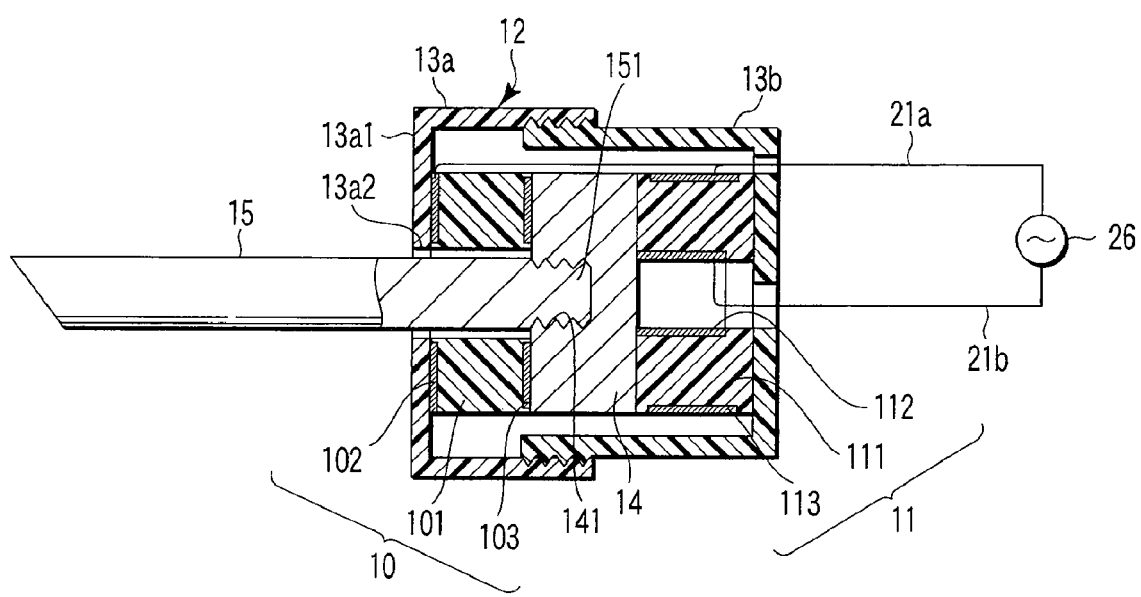
FIG. 8 is a view showing an attaching structure of a blade and a fixing member in a second modification example of the ultrasonic surgical instrument according to the first embodiment.

FIG. 8 shows a second modification example of the ultrasonic surgical instrument 1 according to the first embodiment. In the first embodiment, the configuration where the blade 15 is formed integrally with the blade fixing member 14, but the present invention is not limited to the abovementioned configuration. In the present modification example, a configuration that the blade 15 is fastened to the blade fixing member 14 by a screw is adopted.

A screw hole 141 is formed in the blade fixing member 14 of the present modification example. The screw hole 141 of the blade fixing member 14 is provided so as to extend through an inner space portion of the electrostrictive polymer 101 with a cylindrical shape. A male screw unit 151 is provided on a proximal end of the blade 15. The male screw unit 151 of the blade 15 is provided such that it can be joined to the screw hole 141 of the blade fixing member 14 in a screwing manner. After a proximal end portion of the blade 15 is inserted into the cylindrical inner space portion of the electrostrictive polymer 101 of the first actuator 10, the male screw unit 151 is screwed into the screw hole 141 of the blade fixing member 14 to be fixed thereto.

In the present modification example, an effect similar to that of the ultrasonic surgical instrument 1 according to the first embodiment can be obtained. Further, in the present modification example, such a configuration can be adopted that an insulation tube 16 (FIG. 1) which is not shown in FIG. 8 is interposed between the abovementioned blade 15 and the blade insertion hole 13*a*2 of the first case 13*a* to achieve insulation arrangement. Further, an insulation ring (FIG. 1) may be interposed between the positive electrode 102 of the first case 13*a* of the first actuator 10 to achieve insulation arrangement. In this case, a particularly excellent effect can be obtained when large output is required and high voltage is applied to the first actuator 10 and the second actuator 11.

Figure 9:
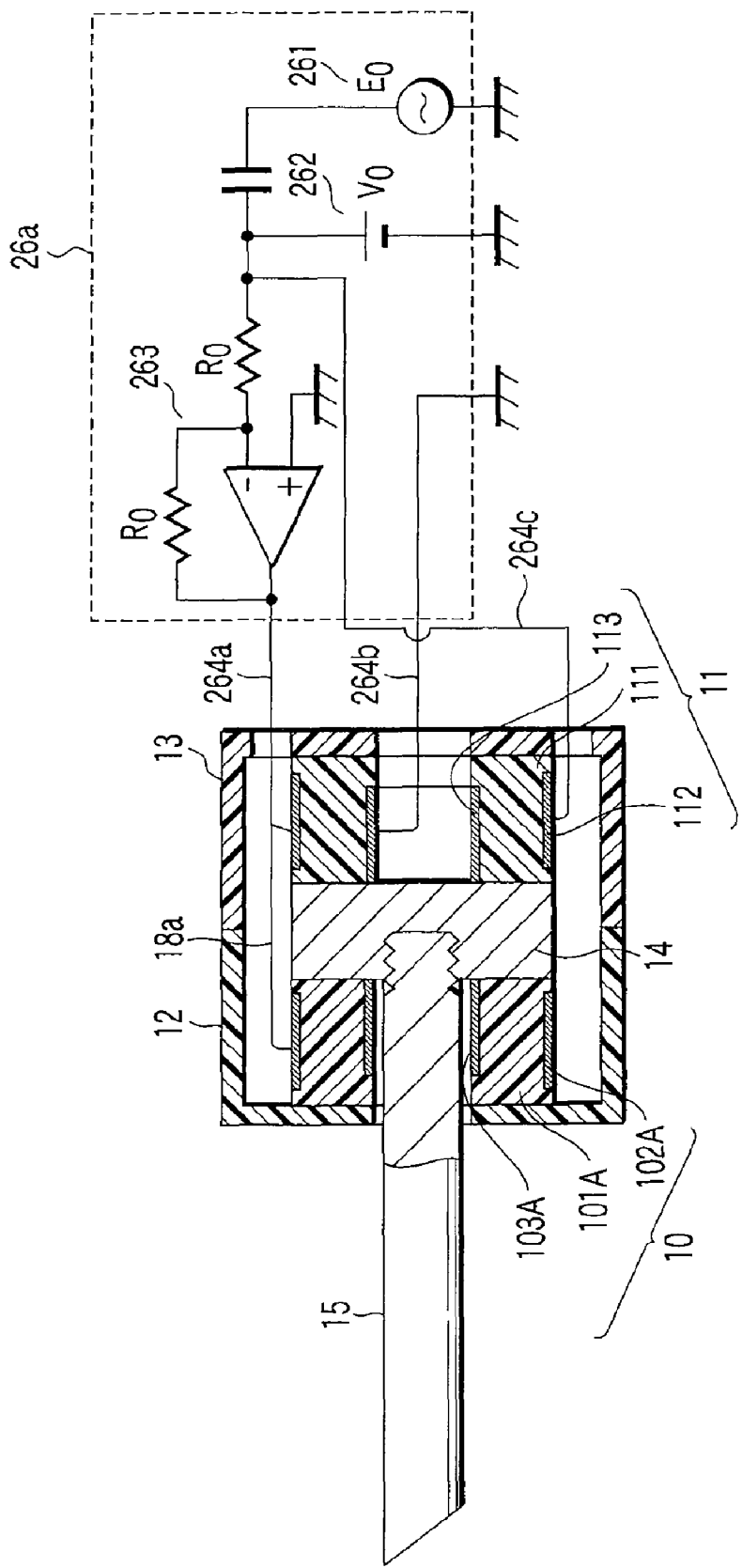
FIG. 9 is view showing a schematic configuration of a third modification example of the ultrasonic surgical instrument according to the first embodiment.

FIG. 9 to FIG. 11C show a third modification example of the ultrasonic surgical instrument 1 according to the first embodiment. In the first embodiment, such a configuration that the first actuator 10 and the second actuator 11 having different electrode structures are used is adopted, but the present invention is not limited to this configuration. In the present modification example, the first actuator 10 and the second actuator 11 have the same electrode structure, as shown in FIG. 9.

That is, the electrode structure shown in FIG. 9 uses an actuator with structure similar to that of the second actuator 11 of the first embodiment as a first actuator 10. In a first actuator 10 of the present modification example, a stretchable and flexible positive electrode 102A is attached to an outer peripheral face of an electrostrictive polymer 101A with a cylindrical shape. Further, a stretchable and flexible negative electrode 103A is attached to an inner peripheral face of the electrostrictive polymer 101A to be separated from the positive electrode 102A. The first actuator 10 is disposed so as to face the second actuator 11 via the blade fixing member 14.

The positive electrode 102A is disposed on the outer peripheral face of the electrostrictive polymer 101A and the negative electrode 103A is disposed on the inner peripheral face of the electrostrictive polymer 111. The negative electrode 103A is electrically connected in a state that it contacts with the blade fixing member 14.

The second actuator 11 is configured in the same manner as the second actuator 11 according to the first embodiment. The positive electrode 112 of the second actuator 11 is electrically connected to the positive electrode 102A of the first actuator 10 via a positive wiring 18a. Similarly, the negative electrode 113 of the second actuator 11 is electrically connected to a negative electrode 103A of the first actuator 10 via the blade fixing member 14.

The respective positive electrodes 102A, 112 of the first and second actuators 10, 11 are arranged so as not to short-circuit the blade fixing member 14. The positive electrode 102A of the first actuator 10 is connected to a power source 26a via a positive wiring 264a. The positive electrode 112 of the second actuator 11 is connected to the power source 26a via a positive wiring 264c.

The respective negative electrodes 103A, 113 of the first and second actuators 10, 11 are arranged in an electrically conductive manner with the blade fixing member 14. The respective negative electrodes 103A, 113 of the first and second actuators 10, 11 are connected to the power source 26a via a negative wiring 264b.

The power source 26a includes an AC power source 261, a bias circuit 262, and an inverting circuit 263. The positive electrodes 102A, 112 of the first and second actuators 10, 11 are wired and connected to the inverting circuit 263 of the power source 26a such that voltages have a phase difference of 180°. That is, since the positive wiring 264a of the first actuator 10 is connected via the inverting circuit 263, there is a phase difference of 180° between voltage of the positive wiring 264a and voltage of the positive wiring 264c of the second actuator 11. Voltages having a phase difference of 180° therebetween are supplied to the first and second actuators 10, 11 via the power source 26a cyclically so that the first and second actuators 10, 11 are driven and controlled.

Figure 10:
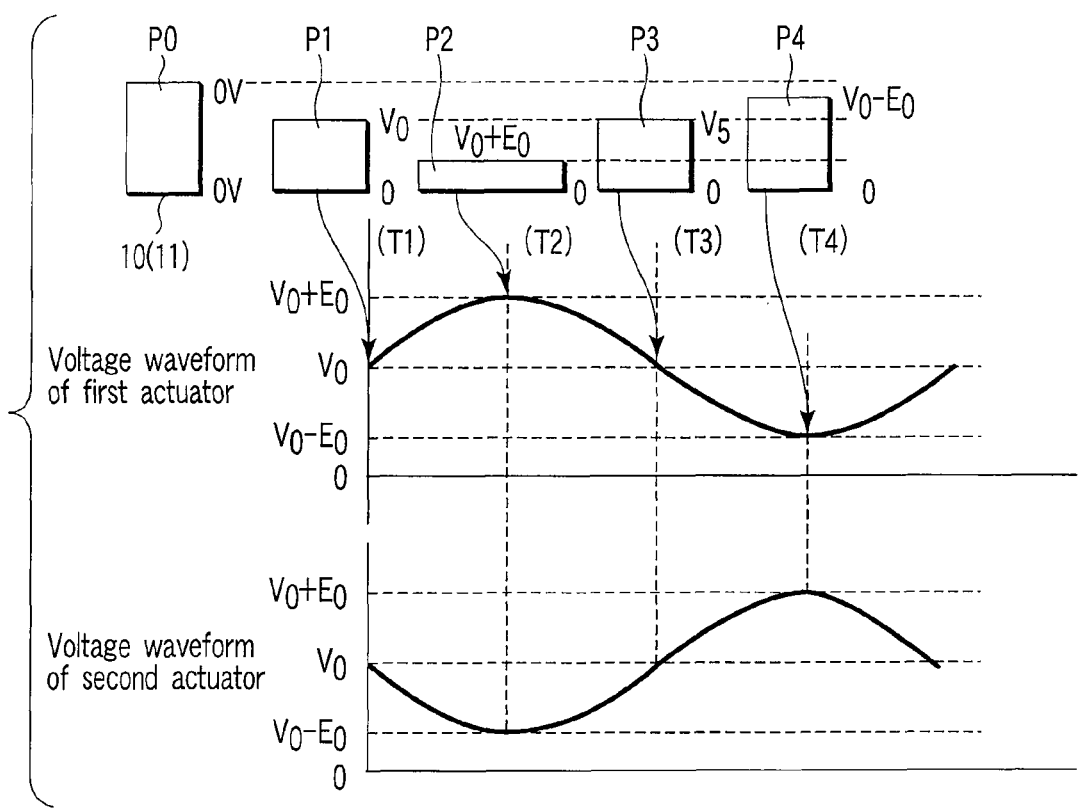
FIG. 10 is an explanatory diagram for explaining a state of voltage application of a first actuator and a state of voltage application of a second actuator in the third modification example.

FIG. 10 is an explanatory diagram for explaining a state of voltage application of the first actuator 10 and a state of voltage application of the second actuator 11 in the present modification example. In FIG. 10, P0 shows a shape of the first and second actuators 10, 11 put in natural states. P1, P3 show shapes of the first and second actuators 10, 11 when bias voltage Vo is applied to the first and second actuators 10, 11 from the power source 26a and AC voltage is 0V (a reference state). P2 shows a shape of the first and second actuators 10, 11 when the first and second actuators 10, 11 have been shrunk by application of voltage (Vo+Eo) thereto from the power source 26a. P4 shows a shape of the first and second actuators 10, 11 when the first and second actuators 10, 11 have been stretched by application of voltage (Vo−Eo) thereto.

The first and second actuators 10, 11 take shapes of P1, P3 which are reference states, respectively, at a time point of T1 at a time of an actuation of the first and second actuators 10, 11. The first actuator 10 is applied with voltage (Vo+Eo) from the power source 26a to be deformed to a shrunk shape of P2 at a time point of T2. At this time, the second actuator 11 is applied with voltage (Vo−Eo) to be deformed to a stretched shape of P4.

The first and second actuators 10, 11 take shapes of P1, P3 corresponding to reference states, respectively, at a time point of T3. The first actuator 10 is applied with voltage (Vo−Eo) from the power source 26a to be deformed to a stretched shape of P4 at a time point of T2. At this time, the second actuator 11 is applied with voltage (Vo+Eo) to be deformed to a shrunk shape of P2.

With the abovementioned configuration, the first and second actuators 10, 11 are set to initial states in a state that voltage from the power source 26a is 0V, as shown in FIG. 11A. The first and second actuators 10, 11 are configured such that, when voltage (Vo−Eo) is applied to the first actuator 10 and voltage (Vo+Eo) is applied to the second actuator 11 via the power source 26a, the first actuator 10 is driven in a shrinking manner and the second actuator 11 is driven in a stretching manner, as shown by arrows in FIG. 11B. When voltage (Vo+Eo) is applied to the first actuator 10 from the power source 26a and voltage (Vo−Eo) is applied to the second actuator 11 therefrom, the first actuator 10 is driven in a stretching manner and the second actuator 11 is driven in a shrinking manner, as shown by arrows in FIG. 11C. Thus, the first and second actuators 10, 11 ultrasonically vibrate the blade 15 in an axial direction in cooperation with each other.

Thereby, an effect similar to that of the first embodiment can be obtained in the present modification example.

Figure 12:
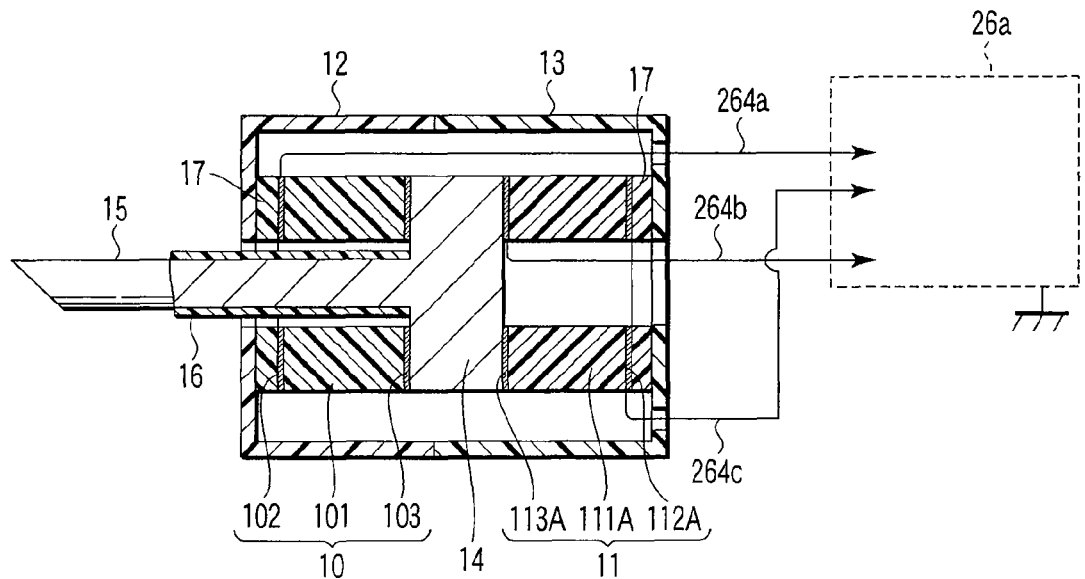
FIG. 12 is a view showing electrode structures of first and second actuators in a fourth modification example of the ultrasonic surgical instrument according to the first embodiment.

FIG. 12 shows a fourth modification example of the ultrasonic surgical instrument 1 according to the first embodiment. In the present modification example, an actuator having a configuration similar to that of the first actuator 10 according to the first embodiment is used as a second actuator 11. In the second actuator 11 of the present modification example, stretchable and flexible positive electrode 112A and negative electrode 113A are attached to both end faces of electrostrictive polymer 111A with a cylindrical shape in a separated state from each other. Here, the positive electrode 112A is disposed on a rear end face of the electrostrictive polymer 111A contacting with the second case 13b, while the negative electrode 113A is disposed on a front end face of the electrostrictive polymer 111A contacting with the blade fixing member 14.

In this case, the negative electrode 103 of the first actuator 10 and the negative electrode 113A of the second actuator 11 are disposed to face each other via the blade fixing member 14, and they are attached to the blade fixing member 14 in an electrically conductive manner therewith.

In the first actuator 10, an insulation ring 17 is interposed between the positive electrode 102 and the first case 13a so that insulation between the first actuator 10 and the first case 13a is maintained. Similarly, in the second actuator 11, an insulation ring 17 is interposed between the positive electrode 112A and the second case 13b so that insulation between the second actuator 17 and the second case 13b is maintained.

The respective positive electrodes 102, 112A of the first and second actuators 10, 11 and the negative electrode 113A of the second actuator 11 are connected to the abovementioned power source 26a like the third modification example (FIG. 9 to FIG. 11C). That is, the positive electrode 102 of the first actuator 10 is connected to the power source 26a via the positive wiring 264a. The positive electrode 112A of the second actuator 11 is connected to the power source 26a via the positive wiring 264c.

The respective negative electrodes 103, 113A of the first and second actuators 10, 11 are disposed so as to be electrically connected to the blade fixing member 14. The respective negative electrodes 103, 113A of the first and second actuators 10, 11 are connected to the power source 26a via the negative wiring 264b.

The positive electrodes 102, 112A of the first and second actuators 10, 11 are wired and connected to the inverting circuit 263 of the power source 26a such that voltages have a phase difference of 180°. That is, since the positive wiring 264a of the first actuator 10 is connected via the inverting circuit 263, there is a phase difference of 180° between voltage of the positive wiring 264a and voltage of the positive wiring 264c of the second actuator 11. Voltages having a phase difference of 180° therebetween are supplied to the first and second actuators 10, 11 via the power source 26a cyclically so that the first and second actuators 10, 11 are driven and controlled.

Incidentally, in the electrode structures shown in FIG. 8, FIG. 9, and FIG. 12, such a configuration may be adopted that a stacked structure where a plurality of positive internal electrodes 104, 114, negative internal electrodes 105, 115, and films of the electrostrictive polymers 101, 111 have been alternately stacked is embedded like the abovementioned first modification example (FIGS. 7A and 7B).

Second Embodiment

Figure 13:
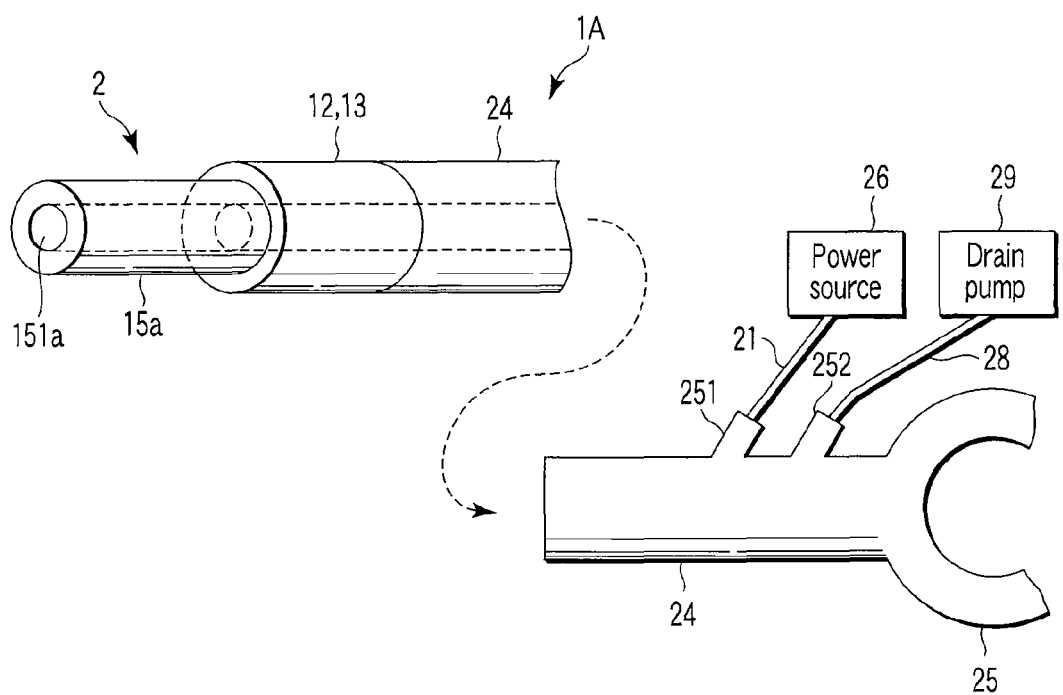
FIG. 13 is a view showing an ultrasonic surgical instrument according to a second embodiment of the present invention.
Figure 14:
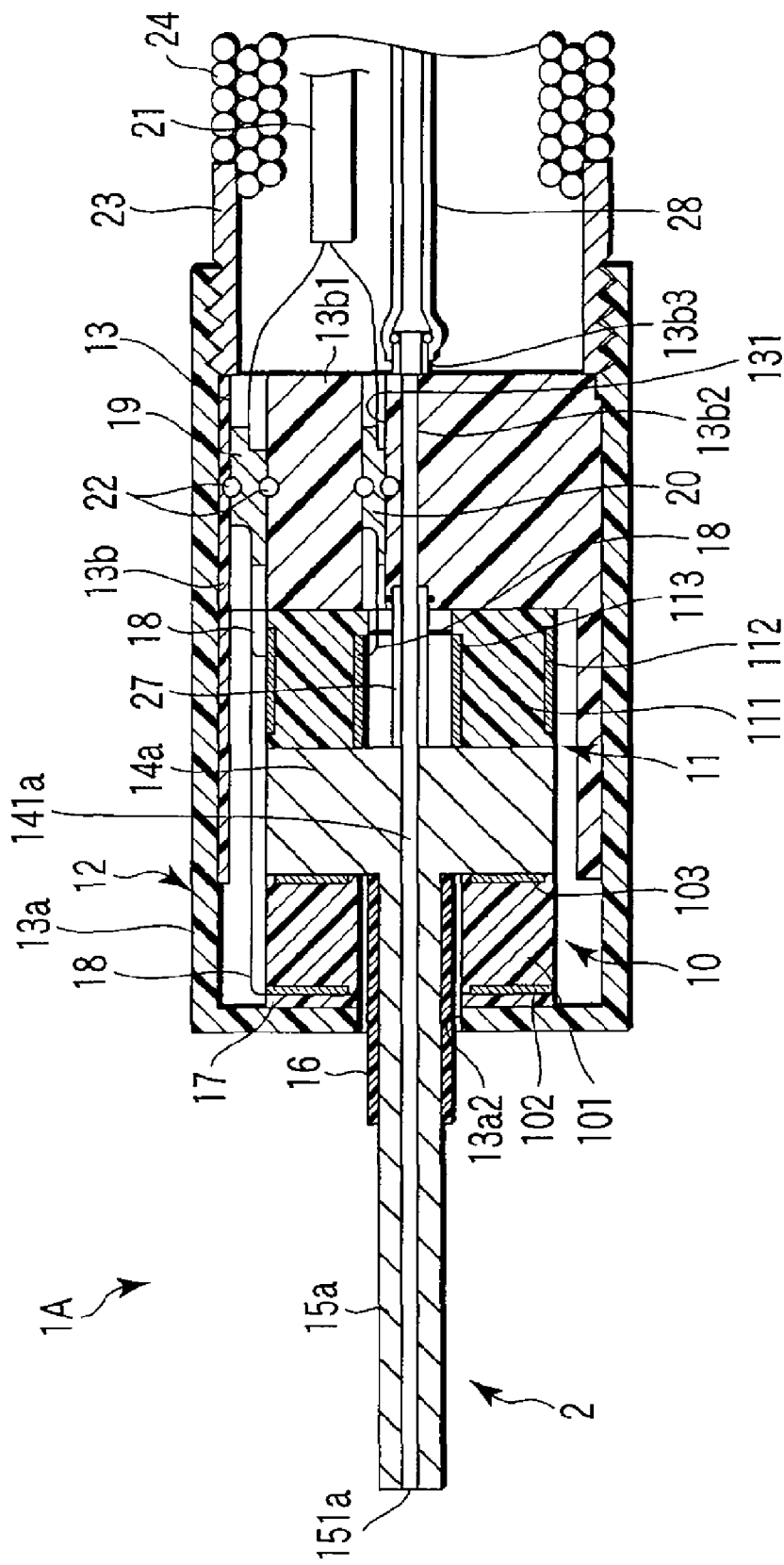
FIG. 14 is an axially sectional view of a main section of the ultrasonic surgical instrument according to the second embodiment of the present invention.

FIG. 13 and FIG. 14 show a second embodiment of the present invention. However, in FIG. 13 and FIG. 14, same portions as those in the first embodiment are attached with same reference numerals and detailed explanation thereof is omitted.

The present embodiment shows an example where the present invention has been applied to an ultrasonic suctioning apparatus 1A carrying out a crushing/emulsifying procedure of a body tissue, as shown in FIG. 13. That is, in the present embodiment, a through-hole 151a is provided at an axial center portion of a blade 15a of a distal end surgical unit 2, and a through-hole 141a is also provided at an axial center portion of a blade fixing member 14a, as shown in FIG. 14.

As shown in FIG. 14, the blade fixing member 14a is interposed between the abovementioned first and second actuators 10, 11. The abovementioned blade 15a is provided on a front end face of the blade fixing member 14a in a projecting manner. A tubular port 27 is provided on a rear end face of the blade fixing member 14a in a projecting manner. The blade 15a is inserted into a cylindrical inner space portion of the abovementioned first actuator 10, and it is further protruded forward from the blade insertion hole 13a2 of a first case 13a.

The abovementioned port 27 is caused to extend through an inner space portion of the cylinder body of the abovementioned second actuator 11. A communication hole 13b2 is provided in the second case 13b so as to face the port 27. The abovementioned port 27 is joined to a front end portion of the communication hole 13b2 via an O-ring (not shown) in a sealing manner.

One end portion of a drain tube 28 is attached to a rear end portion of the communication hole 13b2 via a tubular coupling member 13b3. The drain tube 28 is caused to extend through the sheath 24.

As shown in FIG. 13, a tube drain port 252 is provided on an operation unit 25 adjacent to a wiring cable pulling-out port 251. A proximal end portion of the drain tube 28 is pulled out from the tube drain port 252 of the operation unit 25 to be coupled to a drain pump 29.

Next, an operation of the present embodiment with the abovementioned configuration will be explained. When a crushing/emulsifying procedure of a body tissue is performed using the ultrasonic suctioning apparatus 1A with the abovementioned configuration, the insertion unit 402 of the abovementioned endoscope 401 is first inserted into a body cavity. At this time, an observation image in the body cavity entered through the objective lens 407 of the observation optical system of the endoscope 401 is picked up by the imaging device 409, the image is observed through a screen displayed on a monitor (not shown), and an affected area is confirmed. In a state that the affected area has been confirmed by the endoscope 401, the ultrasonic suctioning apparatus 1A with the abovementioned configuration is inserted into the surgical tool insertion channel 408 through the surgical tool insertion ferrule 413 of the operation unit 403 of the endoscope 401. The blade 15a at the distal end surgical unit 2 of the ultrasonic suctioning apparatus 1A with the abovementioned configuration is protruded from the distal end opening portion 408a of the surgical tool insertion channel 408 to the outside (FIG. 6).

Next, the operation unit 25 is operated while the affected area is being observed, so that the blade 15a is moved back and forth. Thereby, the distal end portion of the blade 15a is caused to approach in accordance with a procedure site. Thereafter, ultrasonic generation operating means (not shown) is operated. Here, voltages from the power source 26 are applied between the respective positive electrodes 102, 112 and the respective negative electrodes 103, 113 in the first and second actuators 10, 11 at a desired cycle, as described above. Thereby, the respective electrostrictive polymers 101, 111 of the first and second actuators 10, 11 are independently driven in a shrinking manner and driven in a stretching manner in synchronism with a supply cycle of voltages from the power source 26. Thereby, the blade 15a is ultrasonically vibrated so that a crushing/emulsifying procedure of a body tissue is performed.

At this time, the drain pump 29 is driven. Therefore, the body tissue which has been subjected to the crushing/emulsifying procedure is suctioned into the through-hole 151a of the blade 15a to be drained from the drain pump 29 to a drain bottle (not shown) via the port 27, the communication hole 13b2, and the tube 28.

Therefore, the following effect can be obtained in the apparatus with the abovementioned configuration. That is, in the ultrasonic suctioning apparatus 1A according to the present embodiment, a blade 15 having high procedure ability can be realized by using the first and second actuators 10, 11 using an electrostrictive polymer actuator like the first embodiment, and a small-sized ultrasonic suctioning apparatus 1A with high procedure ability can be provided.

Incidentally, in the second embodiment, the electrode structures of the respective modification examples explained in the abovementioned first embodiment can be applied to the electrode structures of the first and second actuators 10, 11, and similar effect can be obtained even if the electrode structure is configured by using each of the electrode structures of the modification examples.

Third Embodiment

FIG. 15 to FIG. 18C show a third embodiment of the present invention. Incidentally, in FIG. 15 to FIG. 18C, same portions as those in the first embodiment are attached with same reference numerals, and detailed explanation thereof is omitted.

Figure 15:
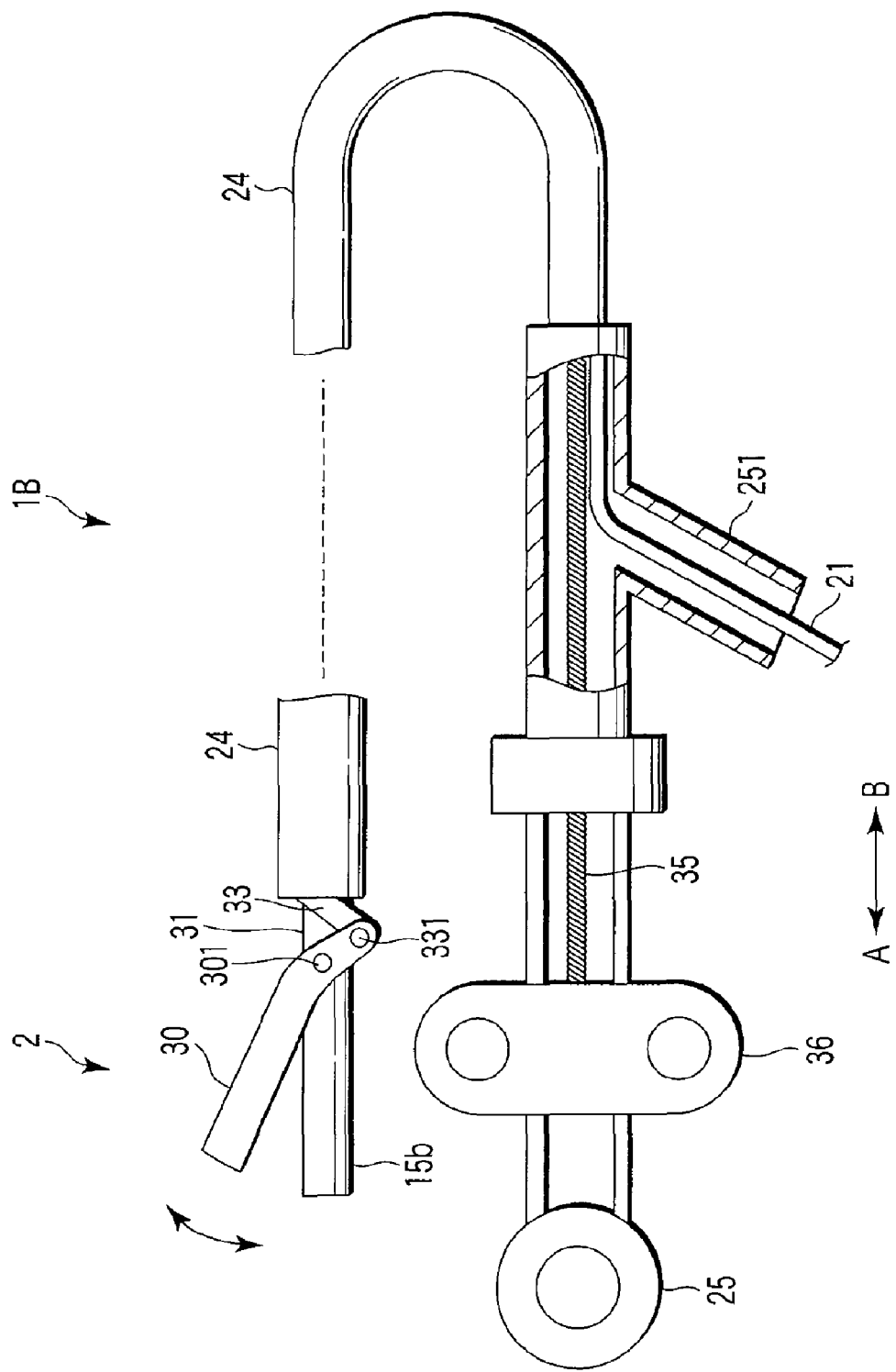
FIG. 15 is a view showing an ultrasonic surgical instrument according to a third embodiment of the present invention.

The present embodiment is an example where the present invention has been applied to an ultrasonic clotting and incising apparatus 1B clipping a body tissue to perform a clopping and incising procedure thereto, as shown in FIG. 15. That is, in the present embodiment, a forceps piece 30 is disposed at a proximal end portion of a blade 15b disposed at a distal end surgical unit 2 in an openable and closable manner.

Figure 16:
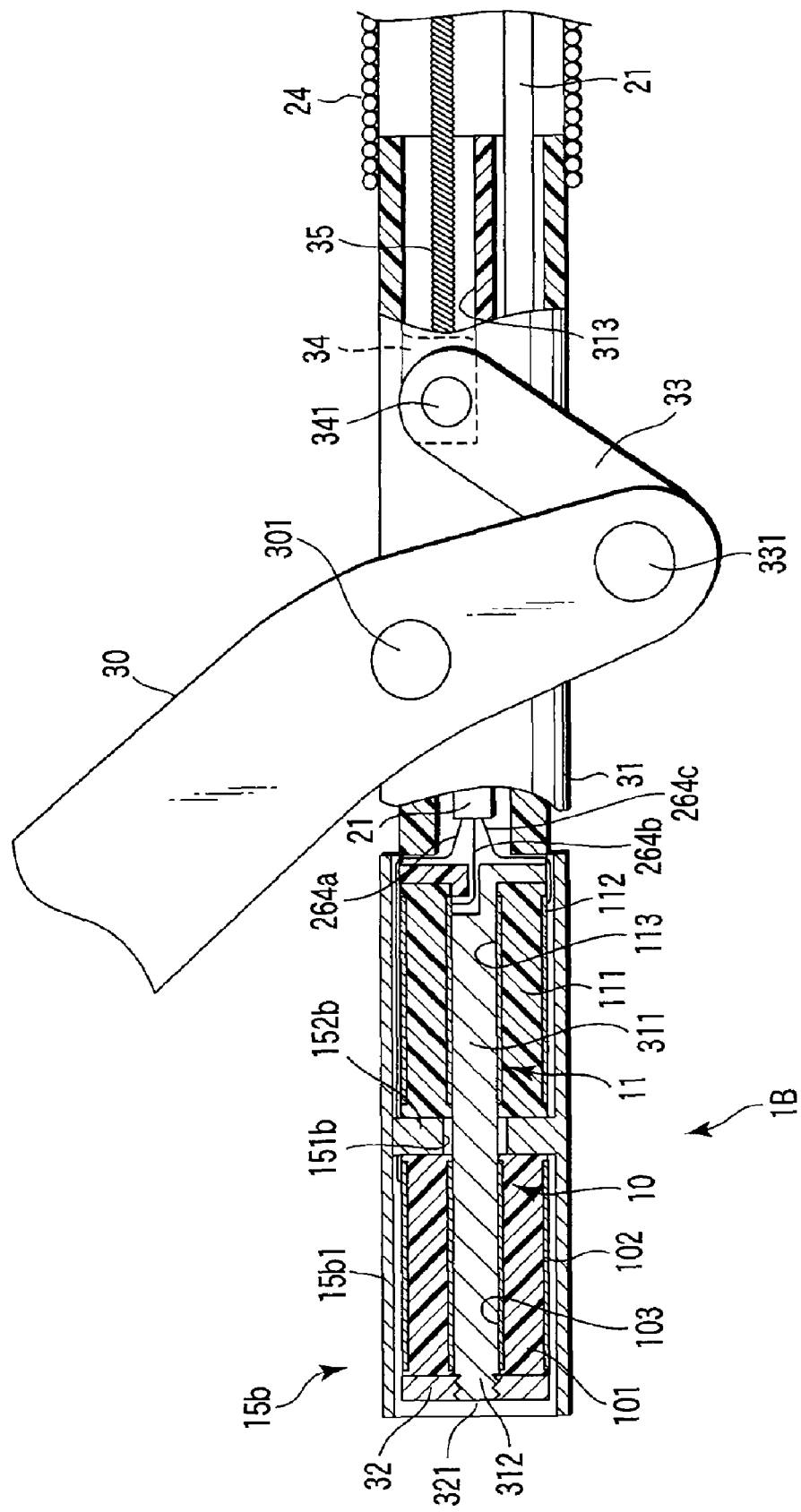
FIG. 16 is a sectional view of a main section of the ultrasonic surgical instrument according to the third embodiment.

A proximal end portion of a cylindrical distal end cover 31 is fixed at a distal end portion of such a sheath 24 as a tightly-wound coil. As shown in FIG. 16, an intermediate portion of the abovementioned forceps piece 30 is rotatably pivoted to a distal end cover 31 via a main shaft pin 301.

A distal end portion of a link member 33 is rotatably attached to a proximal end portion of the forceps piece 30 via a supporting pin 331. A coupling member 34 is rotatably attached to a proximal end portion of the link member 33 via an operation pin 341.

The coupling member 34 is disposed to be movable in an axial direction along a guide groove 313 provided in the distal end cover 31. A distal end portion of an operation wire 35 is attached to the coupling member 34. The operation wire 35 is inserted into the abovementioned sheath 24.

A handle 36 is attached to the operation unit 25 so as to be operable in an axial direction of the operation wire 35 in a sliding manner. A proximal end portion of the operation wire 35 is fixed to the handle 36. The forceps piece 30 is operated to be moved via the operation wire 35 according to a sliding operation of the handle 36 in directions of arrows A and B in FIG. 15.

When the handle 36 is operated toward the near side in a pulling manner so that the operation wire 35 is pulled in a direction of arrow A in FIG. 15, the link member 33 is operated toward the near side via the coupling member 34 and the operation pin 341 in a pulling manner to be rotated in a clockwise direction. Thereby, the forceps piece 30 is rotated about the main shaft pin 301 in a counterclockwise direction. As a result, the forceps piece 30 is moved in a direction of approaching the blade 15b (in a closing direction).

When the abovementioned handle 36 is operated in a pushing-out direction, the abovementioned operation wire 35 is moved in a direction of arrow B in FIG. 15. At this time, the link member 33 is operated via the coupling member 34 and the operation pin 341 in a pushing-out manner to be rotated in a counterclockwise direction. Thereby, the forceps piece 30 is rotated about the main shaft pin 301 in a clockwise direction. As a result, the forceps piece 30 is moved in a direction in which it is separated from the blade 15b (in an opening direction).

Figure 17:
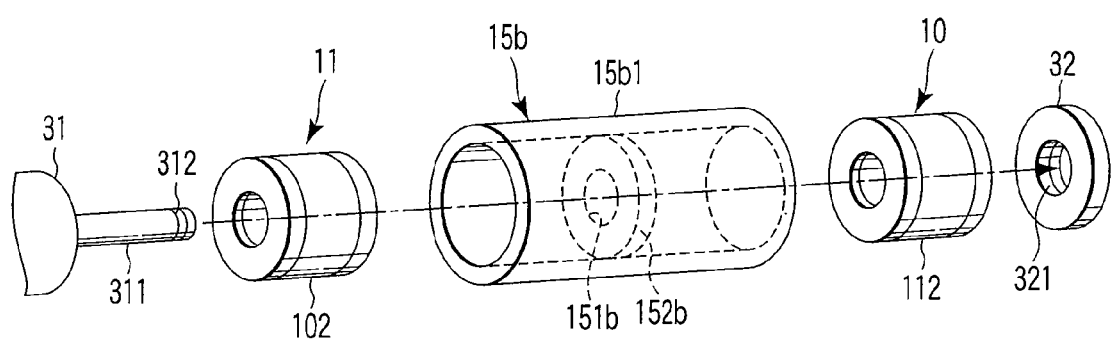
FIG. 17 is an exploded view of the main section of the ultrasonic surgical instrument according to the third embodiment.

As shown in FIG. 16 and FIG. 17, the blade 15b includes a blade main body 15b1 formed in a cylindrical shape. A partition wall 152b is provided in an intermediate portion of the cylinder of the blade main body 15b1. An insertion hole 151b is provided at an axial center portion of the partition wall 152b. Cylindrical first and second actuators 10, 11 are accommodated and disposed in the blade 15b so as to sandwich the partition wall 152b.

The first actuator 10 includes a cylindrical electrostrictive polymer 101, a positive electrode 102 attached on an outer peripheral face of the electrostrictive polymer 101, and a negative electrode 103 attached on an inner peripheral face of the electrostrictive polymer 101. Similarly, the second actuator 11 includes a cylindrical electrostrictive polymer 111, a positive electrode 112 attached on an outer peripheral face of the electrostrictive polymer 111, and a negative electrode 113 attached on an inner peripheral face of the electrostrictive polymer 111.

A fixing shaft unit 311 provided at the distal end cover 31 in a projecting manner is inserted into respective cylindrical inner space portions of the first and second actuators 10, 11 inserted into the abovementioned blade 15b and the insertion hole 151b of the partition wall 152b. A screw unit 312 is provided at a distal end portion of the fixing shaft unit 311. The screw unit 312 is screwed to a screw hole 321 provided in a cover retaining member 32.

Thereby, the first actuator 10 accommodated and disposed in the blade 15b is disposed between the partition wall 152b of the blade 15b and the cover retaining member 32 and the second actuator 11 is disposed between the partition wall 152b of the blade 15b and the distal end cover 31.

The first and second actuators 10, 11 are formed so as to have an electrode structure similar to the third modification example (FIG. 9 to FIG. 11C) of the ultrasonic surgical instrument 1 according to the first embodiment. That is, the first actuator 10 is disposed so as to face the second actuator 11 via the partition wall 152b.

The second actuator 11 is configured in a manner similar to the second actuator 11 of the first embodiment. The positive electrode 112 of the second actuator 11 is electrically connected to the positive electrode 102 of the first actuator 10 via a positive wiring 18a. Similarly, the negative electrode 113 of the second actuator 11 is electrically connected to the negative electrode 103 of the abovementioned actuator 10 via the partition wall 152b.

The respective positive electrodes 102, 112 of the first and second actuators 10, 11 are disposed so as not to short-circuit the partition wall 152b. The positive electrode 102 of the first actuator 10 is connected to the power source 26a via a positive wiring 264a. The positive electrode 112 of the second actuator 11 is connected to the power source 26a via a positive wiring 264c.

The respective negative electrodes 103, 113 of the first and second actuators 10, 11 are disposed so as to be electrically connected to the partition wall 152b. The respective negative electrodes 103, 113 of the first and second actuators 10, 11 are connected to the power source 26a via a negative wiring 264b.

The power source 26a includes an AC power source 261, a biasing circuit 262, and an inverting circuit 263. Positive electrodes 102A, 112 of the first and second actuator 10, 11 are wired and connected to the inverting circuit 263 of the power source 26a such that voltages have a phase difference of 180°. That is, since the positive wiring 264a of the first actuator 10 is connected via the inverting circuit 263, there is a phase difference of 180° between voltage of the positive wiring 264a and voltage of the positive wiring 264c of the second actuator 11. Voltages having a phase difference of 180° therebetween are supplied to the first and second actuators 10, 11 via the power source 26a cyclically so that the first and second actuators 10, 11 are driven and controlled.

The positive wiring 264a of the first actuator 10, the positive wiring 264c of the second actuator 11, and the negative wirings 264b of the first and second actuators 10, 11 are inserted through a wiring cable 21. The wiring cable 21 is connected to the power source 26a. Thereby, in the first and second actuators 10, 11, voltages having a phase difference of 180° are applied between the positive electrodes 102, 112, and the negative electrodes 103, 113 from the power source 26a, as described above. According to an application cycle of the voltages, the first and second actuators 10, 11 are deformed to an initial position shown in FIG. 18A, a state where the first actuator 10 is stretched in an axial direction thereof and the second actuator 11 is shrunk, as shown in FIG. 18B, and a state where the first actuator 10 is shrunk in the axial direction and the second actuator 11 is stretched in the axial direction, as shown in FIG. 18C. Thereby, the blade 15b is ultrasonically vibrated.

Next, an operation of the third embodiment of the abovementioned configuration will be explained. In the ultrasonic clotting and incising apparatus 1B with the abovementioned configuration, when a clotting/incising procedure of a body tissue is performed, the insertion unit 402 of the abovementioned endoscope 401 is first inserted into a body cavity. At this time, an observation image in the body cavity entered through the objective lens 407 of the observation optical system of the endoscope 401 is picked up by the imaging device 409, the image is observed through a screen displayed on a monitor (not shown), and an affected area is confirmed. In a state that the affected area has been confirmed by the endoscope 401, the ultrasonic clotting and incising apparatus 1B with the abovementioned configuration is inserted into the surgical tool insertion channel 408 through the surgical tool insertion ferrule 413 of the operation unit 403 of the endoscope 401. The blade 15b of the distal end surgical unit 2 of the ultrasonic clotting and incising apparatus 1B with the abovementioned configuration is protruded from the distal end opening portion 408a of the surgical tool insertion channel 408 to the outside (FIG. 6).

Next, the operation unit 25 is operated while the affected area is observed, so that the blade 15b is moved back and forth. Thereby, the distal end portion of the blade 15b is caused to approach in accordance with a procedure site. Thereafter, the handle 36 of the operation unit 25 is operated in a pushing-out manner to open the forceps piece 30. In this state, movement and adjustment are performed such that the affected area is positioned between the blade 15b and the forceps piece 30. Subsequently, after a state where the affected area has been positioned between the blade 15b and the forceps piece 30 is confirmed, the handle 36 is operated in a pulling manner. Thereby, the forceps piece 30 is rotated in a closing direction so that a body tissue is held between the forceps piece 30 and the blade 15b.

Next, the operation unit 25 is operated while the holding state is being confirmed, so that voltages having a phase difference of 180° therebetween are applied between the positive electrodes 102, 112 and the negative electrodes 193, 113 of the first and second actuators 10, 11 from the power source 26a at a desired cycle. Thereby, the first and second actuators 10, 11 are deformed to a state where the first actuator 10 is stretched in an axial direction thereof and the second actuator 11 is shrunk in the axial direction, as shown in FIG. 18B and a state where the first actuator 10 is shrunk in the axial direction and the second actuator 11 is stretched in the axial direction, as shown in FIG. 18C in synchronism with a supply cycle of voltages from the power source 26a. Thereby, the blade 15b is ultrasonically vibrated so that a clotting and incising procedure of the body tissue held between the blade 15b and the forceps piece 30 is performed.

Therefore, the apparatus with the abovementioned configuration can achieve the following effect. That is, in the ultrasonic clotting and incising apparatus 1B according to the present embodiment, a blade 15b having high procedure ability can be realized using the first and second actuators 10, 11 using an electrostrictive polymer actuator so that an ultrasonic clotting and incising apparatus 1B reduced in size and having high procedure ability can be provided.

Incidentally, in the ultrasonic clotting and incising apparatus 1B according to the third embodiment, the electrode structures shown in the respective modification examples explained in the abovementioned first embodiment can be used as the electrode structures of the first and second actuators 10, 11, and a similar effect can be obtained even if any one of these electrode structures is used.

The present invention is not limited to the respective embodiments and it can be implemented variously in an implementation stage of the present invention without departing from the gist of the present invention.

Further, the abovementioned embodiments include inventions at various stages and various inventions can be extracted from proper combinations of plural constituent elements disclosed.

For example, even if some constituent elements are removed from all constituent elements shown in the abovementioned embodiments, when the problem to be solved by the invention can be solved and the effect of the present invention can be obtained, a configuration from which the some constituent elements have been removed can be extracted as an invention.

What is claimed is:

1. An ultrasonic surgical instrument including a surgical unit which generates ultrasonic vibration to conduct a procedure of a site to be operated on and driving means for driving the surgical unit, wherein the driving means comprises:
a first actuator provided with a first actuator main body formed of electrostrictive polymer and at least one pair of electrodes which are arranged on the first actuator main body so as to be separated from each other, wherein, when voltage is applied between the electrodes, the electrostrictive polymer is driven in a stretching and shrinking manner;
a second actuator provided with a second actuator main body formed of electrostrictive polymer and at least one pair of electrodes which are arranged on the second actuator main body so as to be separated from each other, wherein, when voltage is applied between the electrodes on the second actuator main body, the electrostrictive polymer of the second actuator main body is driven in a stretching and shrinking manner;
a fixing member which is coupled to the surgical unit; and
power source means for ultrasonically vibrating the surgical unit via the fixing member at a time of driving the first and second actuators, wherein
the surgical unit includes a blade which has a longitudinal axis,
the fixing member is interposed between the first actuator and the second actuator in a longitudinal axial direction of the blade, and
in a first voltage in which the electrostrictive polymer of the first actuator shrinks in a longitudinal axial direction while the electrostrictive polymer of the second actuator stretches in the longitudinal axial direction, and a second voltage in which the electrostrictive polymer of the first actuator stretches in a longitudinal axial direction while the electrostrictive polymer of the second actuator shrinks in the longitudinal axial direction,
the power source means being configured to cyclically apply the first voltage and the second voltage alternately on the first actuator and the second actuator to ultrasonically vibrate the surgical unit via the fixing member.

2. The ultrasonic surgical instrument according to claim 1, wherein
the driving means includes
a casing accommodating the first actuator and the second actuator, and
the first actuator and the second actuator are accommodated in the casing in a stretchable and shrinkable manner.

3. The ultrasonic surgical instrument according to claim 1, wherein
the first actuator includes a first actuator main body formed of electrostrictive polymer with a cylindrical shape and a pair of electrodes disposed on both end portions with the cylindrical shape of the first actuator main body,
the second actuator includes a second actuator main body formed of electrostrictive polymer with a cylindrical shape and a pair of electrodes disposed on an outer peripheral face and an inner peripheral face with the cylindrical shape of the second actuator main body, respectively;
the surgical unit includes a shaft unit inserted into an inner space portion of the cylindrical shape of the first actuator main body of the first actuator, the shaft unit including a distal end portion and a proximal end portion, and the distal end portion contacting with the site to be operated on to conduct a procedure of the site to be operated on, and
the fixing member is interposed between a proximal end portion of the first actuator main body of the first actuator and a distal end portion of the second actuator main body of the second actuator, and the proximal end portion of the shaft unit of the surgical unit is coupled to a shaft center portion of the fixing member.

4. The ultrasonic surgical instrument according to claim 3, wherein
the first actuator includes a first positive electrode disposed on a front end face with the cylindrical shape of the first actuator main body and a first negative electrode disposed on a rear end face with the cylindrical shape of the first actuator main body and fixed in a contacting state with the fixing member,
the second actuator includes a second positive electrode disposed on an outer peripheral face with the cylindrical shape of the second actuator main body and fixed in a non-contacting state with the fixing member, and a second negative electrode disposed on an inner peripheral face with the cylindrical shape of the second actuator main body and fixed in a contacting state with the fixing member,
the second electrode is electrically connected to the first positive electrode via a positive wiring, and
the second electrode is electrically connected to the first negative electrode via the fixing member.

5. The ultrasonic surgical instrument according to claim 1, wherein
the power source means applies AC voltages having a phase difference of 180° between the electrodes of the first actuator and between the electrodes of the second actuator in a synchronizing manner.

6. The ultrasonic surgical instrument according to claim 1, wherein
the first actuator and the second actuator have each a stacked structure where a polymer film formed of electrostrictive polymer and a plurality of inner electrodes are alternately stacked.

7. An ultrasonic surgical instrument comprising:
an insertion unit having a distal end portion and a proximal end portion and configured to be inserted into a channel of an endoscope;
a surgical unit disposed at the distal end portion of the insertion unit and ultrasonically vibrating to conduct a procedure of a site to be operated on; and
driving means for driving the surgical unit, wherein the ultrasonic surgical instrument conducts a procedure of the site to be operated on by ultrasonic vibration of the surgical unit under observation conducted by the endoscope, wherein
the insertion unit is provided with a flexible sheath having a distal end portion and a proximal end portion, the distal end portion of the sheath is connected with the surgical unit,
an operation unit for operating the surgical unit is disposed on the proximal end portion of the sheath, and
the driving means comprises:
a first actuator provided with a first actuator main body formed of electrostrictive polymer and at least one pair of electrodes which are arranged on the first actuator main body so as to be separated from each other to achieve insulation arrangement, wherein, when voltage is applied between the electrodes, the electrostrictive polymer is driven in a stretching and shrinking manner;
a second actuator provided with a second actuator main body formed of electrostrictive polymer and at least one pair of electrodes which are arranged on the second actuator main body so as to be separated from each other to achieve insulation arrangement, wherein, when voltage is applied between the electrodes on the second actuator main body, the electrostrictive polymer of the second actuator main body is driven in a stretching and shrinking manner;
a fixing member which is coupled to the surgical unit; and
power source means for ultrasonically vibrating the surgical unit via the fixing member at a time of driving the first and second actuators, wherein
the surgical unit includes a blade which has a longitudinal axis,
the fixing member is interposed between the first actuator and the second actuator in a longitudinal axial direction of the blade, and
in a first voltage in which the electrostrictive polymer of the first actuator shrinks in a longitudinal axial direction while the electrostrictive polymer of the second actuator stretches in the longitudinal axial direction, and a second voltage in which the electrostrictive polymer of the first actuator stretches in a longitudinal axial direction while the electrostrictive polymer of the second actuator shrinks in the longitudinal axial direction,
the power source means cyclically applies the first voltage and the second voltage alternatel on the first actuator and the second actuator to ultrasonicall vibrate the surgical unit via the fixing member.

* * * * *